United States Patent [19]

Fujita et al.

[11] 4,268,625
[45] May 19, 1981

[54] PHOTOGRAPHIC LIGHT-SENSITIVE ELEMENT FOR THE COLOR DIFFUSION TRANSFER PROCESS

[75] Inventors: Shinsaku Fujita; Hidetoshi Hayashi; Shigetoshi Ono; Yoshinobu Yoshida; Tooru Harada, all of Minami-ashigara, Japan

[73] Assignee: Fuji Photo Film Co., Ltd., Minami-ashigara, Japan

[21] Appl. No.: 100,076

[22] Filed: Dec. 4, 1979

Related U.S. Application Data

[63] Continuation-in-part of Ser. No. 911,571, Jun. 1, 1978, abandoned.

[30] Foreign Application Priority Data

Jun. 1, 1977 [JP] Japan .................................. 52-54533

[51] Int. Cl.$^3$ .......................... G03C 1/40; G03C 1/10
[52] U.S. Cl. ..................................... 430/562; 430/223
[58] Field of Search ............... 430/223, 562, 563, 559

[56] References Cited

U.S. PATENT DOCUMENTS

| | | | |
|---|---|---|---|
| 3,932,381 | 1/1976 | Haase et al. | 430/223 |
| 3,954,476 | 5/1976 | Krutak et al. | 430/223 |
| 4,013,633 | 3/1977 | Haase et al. | 430/223 |
| 4,013,635 | 3/1977 | Landholm et al. | 430/223 |
| 4,055,428 | 10/1977 | Koyama et al. | 430/223 |

Primary Examiner—Richard L. Schilling
Attorney, Agent, or Firm—Sughrue, Rothwell, Mion, Zinn and Macpeak

[57] ABSTRACT

A photographic light-sensitive element for the color diffusion transfer process which comprises a support having thereon at least one light-sensitive silver halide emulsion layer with at least one of the silver halide emulsion layers having associated therewith a dye releasing redox compound represented by the following general formula:

D-Redox Moiety wherein D represents a dye moiety and Redox Moiety represents a group represented by the following general formula (I):

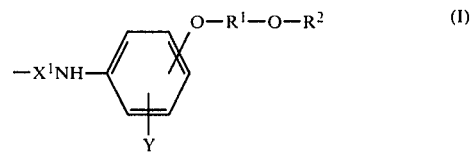

wherein $X^1$ represents an —SO$_2$— group or a —CO— group; $R^1$ represents an unsubstituted straight chain alkylene group having 2 or more carbon atoms or an unsubstituted branched chain alkylene group having 2 or more carbon atoms with the proviso the branched chain alkylene group is incapable of forming an acetal linkage; $R^2$ represents an alkyl group; and Y represents an o- or p-hydroxyarylsulfamoyl group having a ballast group bonded thereto.

15 Claims, No Drawings

PHOTOGRAPHIC LIGHT-SENSITIVE ELEMENT FOR THE COLOR DIFFUSION TRANSFER PROCESS

This is a continuation-in-part of application Ser. No. 911,571, filed June 1, 1978 and now abandoned.

BACKGROUND OF THE INVENTION

1. Field of the Invention

The present invention relates to a photographic light-sensitive element for the color diffusion transfer process and, more particularly, to a silver halide photographic light-sensitive element for the color diffusion transfer process containing a dye releasing redox compound containing a novel redox moiety.

2. Description of the Prior Art

Color diffusion transfer color image forming processes using a dye releasing redox compound are described in U.S. Pat. Nos. 3,928,312, 3,931,144, 3,929,760, 3,932,381, 3,954,476, U.S. Patent Application Document B-351,673, West German Patent Application (OLS) No. 2,505,248, and Research Disclosure, No. 13024 (1957). The term "dye releasing redox compound" means a compound containing therein a group referred to as a redox moiety and a dye (including a dye precursor) moiety. The redox moiety renders the redox compound immobile due to a ballast group attached thereto, but the compound per se splits and releases a compound having the dye moiety (dye compound) due to a redox reaction under alkaline conditions. For instance, a light-sensitive element having a light-sensitive silver halide emulsion layer and a redox compound associated therewith is exposed and developed with an alkaline processing solution, whereby the redox compound per se is oxidized in proportion to the amount of developed silver halide and then splits into a compound having a dye moiety (dye compound) and a nondiffusible quinone compound due to the alkaline processing solution. As a result, the compound having a dye moiety diffuses into an image receiving layer to provide a transferred image therein.

Examples of redox compounds which release cyan dye compounds are described in U.S. Pat. Nos. 3,929,760 and 3,942,987, etc. Examples of redox compounds which release magenta dye compounds are described in U.S. Pat. Nos. 3,954,476, 3,931,144 and 3,932,380, etc. Examples of redox compounds which release yellow dye compounds are described in U.S. Pat. No. 4,013,633, etc. However, using these prior art dye releasing redox compounds, technical problems are encountered in that the transferred images have insufficient stability (for example, the light fastness of the images is not sufficient and the images fade to a large extent under light) and in that the transfer of the dye compounds is not sufficient.

SUMMARY OF THE INVENTION

A first object of the present invention is to provide a dye releasing redox compound which provide a stable dye image (cyan, magenta or yellow dye image).

A second object of the present invention is to provide a dye releasing redox compound having a dye moiety whose hue is excellent.

A third object of the present invention is to provide a dye releasing redox compound having a novel redox moiety which improves the transferability of the dye moiety.

A fourth object of the present invention is to provide a photographic light-sensitive element for the color diffusion transfer process containing a dye releasing redox compound which provides a transferred dye image having a sufficiently high optical density in the presence of a relatively small amount of silver halide.

A fifth object of the present invention is to provide a so-called "negative utilizable" photographic light-sensitive element for the color diffusion transfer process in which a light-sensitive element is also utilized.

It has now been found that the above-described objects are effectively attained by a photographic light-sensitive element with satisfactory photographic properties for the color diffusion transfer process which comprises a support having thereon at least one light-sensitive silver halide emulsion layer with at least one silver halide emulsion layer having associated therewith a dye releasing redox compound represented by the following general formula:

D-Redox Moiety wherein D represents a dye moiety and Redox Moiety represents a group represented by the following general formula (I):

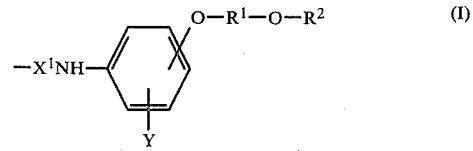

wherein $X^1$ represents an $-SO_2-$ group or a $-CO-$ group; $R^1$ represents an unsubstituted straight chain alkylene group having 2 or more carbon atoms or an unsubstituted branched chain alkylene group having 2 or more carbon atoms with the proviso the branched chain alkylene group is incapable of forming an acetal linkage; $R^2$ represents an alkyl group; and Y represents an o- or p-hydroxyarylsulfamoyl group having a ballast group bonded thereto.

DETAILED DESCRIPTION OF THE INVENTION

In the above-described general formula, the dye releasing redox compound of this invention is characterized by the structure of the redox moiety, in particular, the presence of the $-O-R^1-O-R^2$ group. Due to the presence of the $-O-R^1-O-R^2$ group in the dye-releasing redox compound, the light fastness of the transferred dye compound is improved, the transferability is improved and the advantages in preparation of the compound described hereinafter are attained according to the present invention. In more detail, the improvement in transferability is based on the fact that the activity of the redox moiety is increased and consequently, the dye compound is efficiently released from the dye-releasing redox compound due to the presence of the above-described $-O-R^1-OR^2$ group.

Although the details of the reasons for the improvement in light fastness are still unclear, while not desiring to be bound it is believed that it arises due to the association and the steric conformation of the dye compound transferred and due to the affinity to a mordant of the transferred dye compound in an image receiving layer.

In this connection, the effects due to the $-O-R^1-O-R^2$ group are neither disclosed nor suggested in the prior art (for example, the above-described prior art patents). This is further explained with reference to the following specific example. The redox compounds described in West German Patent Application (OLS) No. 2,505,248 described above are compounds containing therein an

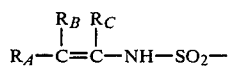

group (redox moiety) and an X' group (dye moiety) with a compound of the formula shown below being a specific example

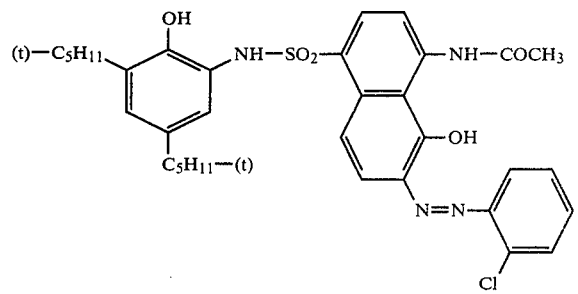

Therefore, the redox moieties of the prior art are completely distinguished from the redox moiety represented by the general formula (I) of the present invention.

The dye releasing redox compounds affording to the present invention are described in greater detail below.

For $X^1$, an $-SO_2-$ group is preferred.

The alkylene group having 2 to 15 carbon atoms represented by $R^1$ can be a straight chain or branched chain alkylene group and an alkylene group having 2 to 8 carbon atoms is preferred. Although $R^1$ can be a branched chain alkylene group, a branched chain alkylene group which forms an acetal linkage is excluded. Particularly preferred examples of $R^1$ are a straight chain alkylene group represented by the formula $-(CH_2)_p-$, wherein p is an integer of 2 to 4, and a branched chain alkylene group having 3 to 4 carbon atoms such as $-CH(CH_3)CH_2-$ and $-CH_2CH_2CH(CH_3)-$ with an alkylene group which forms an acetal linkage being excluded as described above. In view of easy availability of starting materials to produce the dye-releasing redox compounds of this invention, a $-CH_2CH_2-$ group is particularly advantageous for $R^1$. When $R^1$ represents a methylene group, an acetal linkage, such as $-O-CH_2-O-R^2$, is formed, which is undesirable since it is chemically unstable (particularly under acidic conditions) and tends to decompose during the preparation thereof. For the same reason, groups where two oxygen atoms are bonded to the same carbon atom in the $-O-R^1-O-R^2$ group (i.e., forming an acetal linkage), are also not desirable.

The alkyl group represented by $R^2$ can be an unsubstituted or substituted straight chain or branched chain alkyl group and preferably is an alkyl group having 1 to 8 carbon atoms. From the standpoint of the preparation of the redox compounds of this invention, an unsubstituted alkyl group is preferred. A particularly preferred example of $R^2$ is a straight chain or branched chain alkyl group having 1 to 4 carbon atoms (for example, a methyl group, an ethyl group, an n-propyl group, an isopropyl group, an n-butyl group, etc.). Suitable substituents which can be present on the alkyl group for $R^2$ include, for example, one or more of a straight or branched chain alkoxy group having 1 to 8 carbon atoms (for example, a methoxy group, an ethoxy group, etc.), a dialkylamino group (each alkyl moiety of which can be a straight chain or branched chain alkyl moiety and can have 1 to 8 carbon atoms, for example, a diethylamino group, etc.), and the like.

The dye moiety represented by D includes a residue of a dye such as an azo dye, an azomethine dye, an indoaniline dye, an indophenol dye, an anthraquinone dye, a triarylmethane dye, an alizarin dye, a merocyanine dye, a nitro dye, a quinoline dye, a cyanine dye, an indigoid dye, a phthalocyanine dye, a metal complex dye, and the like.

An azo dye residue is particularly preferred for the dye moiety. Most particularly, an azo dye residue represented by the following formula (IIa) or (IIb) is preferred.

wherein A represents a coupling component residue (for example, a residue derived from a phenol or nucleus-substituted phenol, a 1- or 2-naphthol or a nucleus-substituted 1- or 2-naphthol, a pyrazolone or a nucleus-substituted pyrazolone, an acyclic or alicyclic β-diketone compound, etc.); and B represents a phenyl group or a nucleus-substituted phenyl group or a naphthyl group or a nucleus-substituted naphthyl group.

The term "coupling component" as used herein is well known in the dye art and means a compound capable of undergoing a coupling reaction with a diazonium compound. Coupling components are described in greater detail in Hiroshi Horiguchi, *Sosetsu Gosei Senryo* (Synthetic Dyes), pp. 110 to 112 and 124 to 129, Sankyo Publisher, Tokyo (1968); Yutaka Hosoda, *Riron Seizo Senryo Kagaku* (Theory of Manufactured Dye Chemistry), pp. 144 to 149, Gihodo Publisher, Tokyo (1957); the Society of Dyers and Colourists, *Colour Index*, 3rd Ed., Vol. 4, pp. 4009 to 4013; and H. A. Lubs, *The Chemistry of Synthetic Dyes and Pigments*, pp. 101 to 109, Waverly Press Inc., Baltimore (1955). In the present invention, a group A which is derived from a coupling component of the formula A-H is designated a coupling component residue. Of coupling components of the formula A-H, a phenol or a nucleus-substituted phenol, a 1- or 2-naphthol or a nucleus-substituted 1- or 2-naphthol, a pyrazolone or a nucleus-substituted pyrazolone, and an acyclic or alicyclic β-diketone compound are particularly preferred. The coupling position of these coupling components of the formula A-H is also well known in the dye art. In formula (IIa) or (IIb), the azo group ($-N=N-$) is bonded at the coupling position to A. For example, the coupling position in a phenol or a nucleus-substituted phenol is in the ortho or para position to the hydroxy group. The coupling position in a 1-naphthol or a nucleus-substituted 1-naphthol is in the 4- or 2-position, while the coupling position in a 2-naphthol or a nucleus-substituted 2-naphthol is in the 1-position. The coupling position in a pyrazolone or a nucleus-substituted pyrazolone is in the 4-position of the pyrazolone ring. The coupling position of an acyclic or alicyclic β-diketone compound is at the methylene group attached to both carbonyl groups (the so-called active methylene group). A phenyl group or a nucleus-substituted phenyl group is particularly preferred for B, since such a group advantageously influences the transferability of the released dye compound.

In one preferred embodiment, the dye residue of the formula (IIb) is represented by the following formula (III):

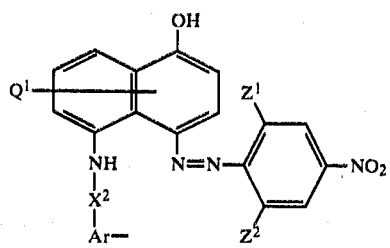

wherein $Q^1$, which can be present on either ring of the naphthol nucleus, represents a hydrogen atom, a halogen atom (e.g., a chlorine atom or a bromine atom), a sulfamoyl group represented by the formula $-SO_2NR^3R^4$, a group represented by the formula $-SO_2R^5$, a carboxy group, a group represented by the formula $-COOR^6$, or a group represented by the formula $-CONR^3R^4$, wherein in the above groups, $R^3$ represents a hydrogen atom or a straight or branched chain alkyl group having 1 to 8 carbon atoms, which may be substituted, $R^4$ represents a hydrogen atom, or a straight or branched chain alkyl group having 1 to 8 carbon atoms, which may be substituted, a straight or branched chain aralkyl group having 7 to 12 carbon atoms or a phenyl group which may be substituted, and $R^3$ and $R^4$ may combine directly or through an oxygen atom to form a ring (preferably a 5- to 8-membered ring, for example, morpholino, piperidino, pyrrolidino, etc.), $R^5$ represents a straight or branched chain alkyl group having 1 to 8 carbon atoms, which may be substituted, or a straight or branched chain aralkyl group having 7 to 12 carbon atoms which may be substituted, and $R^6$ represents a straight or branched chain alkyl group having 1 to 8 carbon atoms which may be substituted or a phenyl group which may be substituted; $X^2$ represents $-SO_2-$ or $-CO-$; Ar represents a phenylene group which may be substituted; $Z^1$ represents a halogen atom (e.g., a chlorine atom or a bromine atom), a cyano group, a nitro group, a trifluoromethyl group, a straight or branched chain alkyl group having 1 to 8 carbon atoms which may be substituted, a straight or branched chain alkoxy group having 1 to 8 carbon atoms which may be substituted, a carboxy group, a carboxylic acid ester group represented by the formula $-COOR^6$, a fluorosulfonyl group, a phenoxysulfonyl group which may be substituted, a sulfamoyl group represented by the formula $-SO_2NR^3R^4$, a carbamoyl group represented by the formula $-CONR^3R^4$, a straight or branched chain alkylsulfonyl group having 1 to 8 carbon atoms in which the alkyl moiety may be substituted, a phenylsulfonyl group which may be substituted, wherein, in the above groups, $R^3$, $R^4$ and $R^6$ each has the same meaning as defined above; $Z^2$ represents a hydrogen atom, a halogen atom (e.g., a chlorine atom or a bromine atom), a nitro group, a cyano group or a trifluoromethyl group.

In the sulfamoyl group represented by the formula $-SO_2NR^3R^4$ for $Q^1$, $R^3$ is preferably a hydrogen atom, an unsubstituted alkyl group having 1 to 4 carbon atoms (e.g., a methyl group, an ethyl group, a propyl group; an isopropyl group, a butyl group, a t-butyl group, etc.) or a substituted alkyl group having 1 to 4 carbon atoms in the alkyl moiety, and $R^4$ is preferably a hydrogen atom, an unsubstituted alkyl group having 1 to 4 carbon atoms (e.g., a methyl group, an ethyl group, a propyl group, an isopropyl group, a butyl group, a t-butyl group, etc.), a substituted alkyl group having 1 to 4 carbon atoms in the alkyl moiety, a benzyl group, an unsubstituted phenyl group, or a substituted phenyl group having 6 to 9 carbon atoms. Also, $R^3$ and $R^4$ may be combine directly or through an oxygen atom to form a 5- or 6-membered ring. In particular, (1) where $R^3$ and $R^4$ each represents a hydrogen atom and (2) where one of $R^3$ and $R^4$ represents a hydrogen atom and the other of $R^3$ and $R^4$ represents an alkyl group having 1 to 4 carbon atoms, are preferred because of easy availability of the starting materials and excellent transferability of the dye compound formed. The same situation exists for the $-CONR^3R^4$ group.

With respect to the $-SO_2R^5$ group, $R^5$ preferably represents an unsubstituted alkyl group having 1 to 4 carbon atoms (e.g., a methyl group, an ethyl group, a propyl group, an isopropyl group, a butyl group, a t-butyl group, etc.), a substituted alkyl group having 1 to 4 carbon atoms in the alkyl moiety or a benzyl group. In particular, an alkyl group having 1 to 4 carbon atoms and a benzyl group are preferred because of easy availability of the starting materials and excellent transferability of the dye compound formed. In case of the $-COOR^6$ group, $R^6$ preferably represents an unsubstituted alkyl group having 1 to 4 carbon atoms (e.g., a methyl group, an ethyl group, a propyl group, an isopropyl group, a butyl group, a t-butyl group, etc.), a substituted alkyl group having 1 to 4 carbon atoms in the alkyl moiety, an unsubstituted phenyl group or a substituted phenyl group having 6 to 9 carbon atoms.

Examples of suitable substituents which can be present in the above-described substituted alkyl groups represented by $R^3$ to $R^6$ include one or more of a cyano group, a straight or branched chain alkoxy group having 1 to 4 carbon atoms (e.g., a methoxy group, an ethoxy group, etc.), a hydroxy group, a carboxy group, a sulfo group, etc. Examples of suitable substituents which can be present in the above-described substituted phenyl group represented by $R^4$ or $R^6$ include one or more of a hydroxy group, a halogen atom (e.g., a chlorine atom or a bromine atom), a carboxy group, a sulfo group, a sulfamoyl group, etc.

Examples of suitable substituents which can be present in the above-described substituted phenylene group represented by Ar include one or more of a carboxy group, a halogen atom (e.g., a chlorine atom or a bromine atom), a straight or branched chain alkyl group having 1 to 4 carbon atoms (e.g., a methyl group, an ethyl group, a propyl group, an isopropyl group, a butyl group, a t-butyl group, etc.), a straight or branched chain alkoxy group having 1 to 4 carbon atoms (e.g., a methoxy group, an ethoxy group, a propoxy group, etc.), etc.

The alkyl group represented by $Z^1$ may be a straight chain or branched chain alkyl group and is preferably an alkyl group having 1 to 8 carbon atoms (more preferably 1 to 4 carbon atoms, e.g., a methyl group, an ethyl group, a propyl group, an isopropyl group, a butyl group, a t-butyl group, etc.). The alkoxy group represented by $Z^1$ may be a straight chain or branched chain alkoxy group and is preferably an alkoxy group having 1 to 8 carbon atoms (more preferably 1 to 4 carbon atoms, e.g., a methoxy group, an ethoxy group, a propoxy group, etc.).

Preferred examples of —SO$_2$NR$^3$R$^4$ and —CONR$^3$R$^4$ groups represented by Z$^1$ are the same as those described for Q$^1$ above.

The alkylsulfonyl group represented by Z$^1$ may be a straight chain or branched chain alkylsulfonyl group and is preferably an alkylsulfonyl group having 1 to 8 carbon atoms (more preferably 1 to 4 carbon atoms, e.g., a methylsulfonyl group, an ethylsulfonyl group, etc.). Examples of suitable substituents which can be present in the substituted alkylsulfonyl group (preferably having 1 to 8 carbon atoms, more preferably 1 to 4 carbon atoms in the alkyl moiety) represented by Z$^1$ include one or more of a cyano group, an alkoxy group having 1 to 4 carbon atoms (e.g., a methoxy group, an ethoxy group, a propoxy group, etc.); a hydroxy group, a carboxy group, a sulfo group, etc. Examples of suitable substituents which can be present in the substituted phenoxysulfonyl group and the substituted phenylsulfonyl group represented by Z$^1$ include one or more of a hydroxy group, a halogen atom (e.g., a chlorine atom or a bromine atom), a carboxy group, a sulfo group, a sulfamoyl group, etc.

In another preferred embodiment, the dye residue of the formula (IIa) is represented by the following formula (IV):

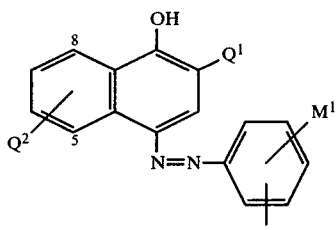

(IV)

wherein Q$^1$ has the same meaning as defined in the formula (III); Q$^2$, which is positioned at the 5- or the 8-position to the hydroxy group, represents a hydroxy group, an —NHCOR$^4$ group or an —NHSO$_2$R$^4$ group, wherein R$^4$ has the same meaning as defined in the formula (III) except that R$^4$ is not a hydrogen atom; M$^1$ represents a hydrogen atom, a straight or branched chain alkyl group having 1 to 8 carbon atoms which may be substituted, a straight or branched chain alkoxy group having 1 to 8 carbon atoms or a halogen atom (e.g., a chlorine atom or a bromine atom).

The unsubstituted alkyl group represented by M$^1$ is preferably an unsubstituted alkyl group having 1 to 8 carbon atoms (more preferably 1 to 4 carbon atoms, e.g., a methyl group, an ethyl group, a propyl group, an isopropyl group, a butyl group, a t-butyl group, etc.). The substituted alkyl group represented by M$^1$ is a substituted alkyl group having 1 to 8 carbon atoms (more preferably 1 to 4 carbon atoms) in the alkyl moiety. Examples of suitable substituents which can be present in the substituted alkyl group are one or more of preferably those described above for the substituted alkyl group for R$^3$ to R$^6$. The alkoxy group represented by M$^1$ is preferably an alkoxy group having 1 to 8 carbon atoms (more preferably 1 to 4 carbon atoms, e.g., a methoxy group, an ethoxy group, a propoxy group, etc.).

In still another preferred embodiment, the dye residue of the formula (IIa) is represented by the following formula (V):

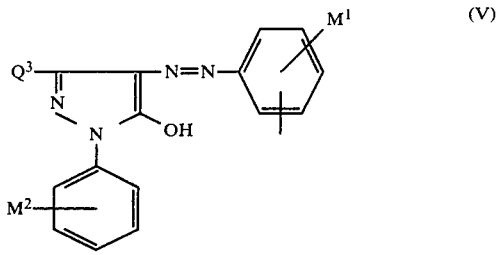

(V)

wherein M$^1$ has the same meaning as defined in the formula (IV); M$^2$ represents a hydrogen atom, a straight or branched chain alkyl group having 1 to 8 carbon atoms which may be substituted, a sulfamoyl group represented by the formula —SO$_2$NR$^3$R$^4$, wherein R$^3$ and R$^4$ each has the same meaning as defined in the formula (III) above, or a group represented by the formula —COOR$^6$, wherein R$^6$ has the same meaning as defined in the formula (III) above; and Q$^3$ represents a cyano group or a carbamoyl group represented by the formula —CONR$^3$R$^4$, wherein R$^3$ and R$^4$ each has the same meaning as defined in the formula (III) above.

The unsubstituted alkyl group or the substituted alkyl group represented by M$^2$ is preferably an unsubstituted alkyl group having 1 to 4 carbon atoms (e.g., a methyl group, an ethyl group, a propyl group, an isopropyl group, a butyl group, a t-butyl group, etc.) or a substituted alkyl group having 1 to 4 carbon atoms in the alkyl moiety. Examples of suitable substituents which can be present in the substituted alkyl group are one or more of those as described above for the substituted alkyl group for R$^3$ to R$^6$.

Preferred sulfamoyl groups substituted with an o- or p-hydroxyaryl group having a ballast group bonded thereto represented by Y in the formula (I) are represented by the general formula (VI):

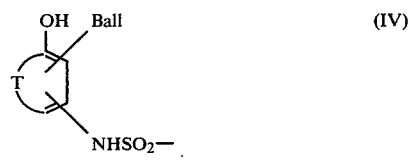

(IV)

wherein Ball represents a ballast group; T represents the carbon atoms necessary to complete a benzene ring, which may be unsubstituted or substituted or condensed with a saturated 5 to 7 membered ring, or a naphthalene ring, which may be unsubstituted or substituted; the —NHSO$_2$— group is present at the o- or p-position to the hydroxy group; and when T represents the atoms necessary to complete a naphthalene ring, Ball can be bonded to either of the two rings. More preferred groups represented by the general formula (VI) are sulfamoyl groups substituted with an o-hydroxyphenyl group having a ballast group bonded thereto, which phenyl group may be substituted as described above, or with a p-hydroxynaphthyl group having a ballast group bonded thereto.

Examples of suitable substituents which can be present on the benzene ring or the naphthalene ring include, for example, one or more of a straight or branched chain alkyl group (preferably an alkyl group having 1 to 8 carbon atoms, and more preferably an alkyl group having 1 to 4 carbon atoms, e.g., a methyl group, an ethyl group, a propyl group, an isopropyl group, a butyl group, a t-butyl group, etc.) or a halogen atom (such as a chlorine atom, etc.).

The ballast group, Ball, is an organic ballast group capable of rendering the dye-releasing redox compound non-diffusible during development in an alkaline processing solution and preferably is or contains a hydrophobic residue having 8 to 32 carbon atoms. This organic ballast group can be bonded to the dye-releasing redox compound directly or through a linking group, for example, an imino bond, an ether bond, a thioether bond, a carbonamido bond, a sulfonamido bond, a ureido bond, an ester bond, an imido bond, a carbamoyl bond, a sulfamoyl bond, etc.

Specific examples of ballast groups are illustrated below:
an alkyl group or an alkenyl group (for example, a dodecyl group, a hexadecyl group, an octadecyl group, etc.), an alkoxyalkyl group (for example, a 3-(octyloxy)propyl group, a 3-(2-ethylundecyloxy)propyl group, etc., as described in Japanese Patent Publication No. 27563/1964, etc.), an alkylaryl group (for example, a 4-nonylphenyl group, a 2,4-di-tert-butylphenyl group, etc.), an alkylaryloxyalkyl group (for example, a 2,4-di-tert-pentylphenoxymethyl group, an α-(2,4-di-tert-pentylphenoxy)propyl group, a 1-(3-pentadecylphenoxy)ethyl group, etc.), an acylamidoalkyl group (for example, a group described in U.S. Pat. Nos. 3,337,344 and 3,418,129, a 2-(N-butylhexadecanamido)ethyl group, etc.), an alkoxyaryl or aryloxyaryl group (for example, a 4-(n-octadecyloxy)phenyl group, a 4-(4-n-dodecylphenyloxy)phenyl group, etc.), a residue containing both an alkyl or alkenyl long-chain aliphatic group and a water-solubilizing group such as a carboxy group or a sulfo group (for example, a 1-carboxymethyl-2-nonadecenyl group, a 1-sulfoheptadecyl group, etc.), an alkyl group substituted with an ester group (for example, a 1-ethoxycarbonylheptadecyl group, a 2-(n-dodecyloxycarbonyl)ethyl group, etc.), an alkyl group substituted with an aryl group or a heterocyclic group (for example, a 2-[4-(3-methoxycarbonylheneicosanamido)phenyl]ethyl group, a 2-[4-(2-n-octadecylsuccinimido)phenyl]ethyl group, etc.), and an aryl group substituted with an aryloxy alkoxycarbonyl group (for example, a 4-[2-(2,4-di-tert-pentylphenoxy)-2-methylpropyloxycarbonyl]phenyl group, etc.)

Of the above-described organic ballast groups, those bonded to a bridging group as represented by the following general formulae (VII) to (X) are particularly preferred.

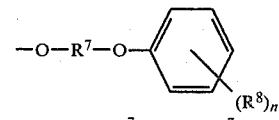   (VIIa)

—CONH—R⁷—O—R⁹   (VIIb)
—CONHR⁹   (VIIc)
—O—R¹⁰   (VIIIa)

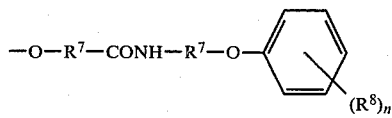   (VIIIb)

—O—R⁷—CONHR⁷   (IXa)

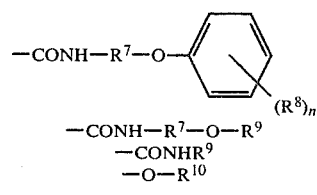   (IXb)

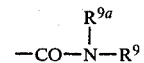   (X)

wherein R⁷ represents a straight or branched chain alkylene group having 1 to 10 carbon atoms, preferably 1 to 6 carbon atoms (such as a propylene group, a butylene group, etc.); R⁸ represents a hydrogen atom or a straight or branched chain alkyl group having 1 to 10 carbon atoms, preferably 1 to 6 carbon atoms (such as a tert-amyl group, etc.); n represents an integer of 1 to 5 (preferably 1 to 2); R⁹ represents a straight or branched chain alkyl group having 4 to 30 carbon atoms, preferably 10 to 20 carbon atoms (such as a dodecyl group, a tetradecyl group, a hexadecyl group, etc.); and R¹⁰ represents a straight or branched chain alkyl group having 8 to 30 carbon atoms, preferably 10 to 20 carbon atoms (such as a hexadecyl group, an octadecyl group, etc.), R⁹ᵃ represents a hydrogen atom or a straight or branched alkyl group having 1 to 30 carbon atoms, preferably 1 to 20 carbon atoms such as a hexadecyl group, an octadecyl group, etc.) or a substituted alkyl group having 8 or more carbon atoms in which the alkyl moiety has 1 or more carbon atoms, with examples of suitable substituents being one or more of, for example, a carbamoyl group, etc.

Specific examples of the sulfamoyl groups represented by the formula (VI) are illustrated below:

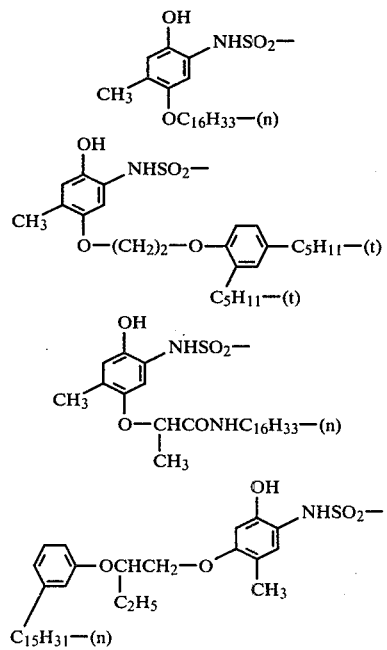

-continued
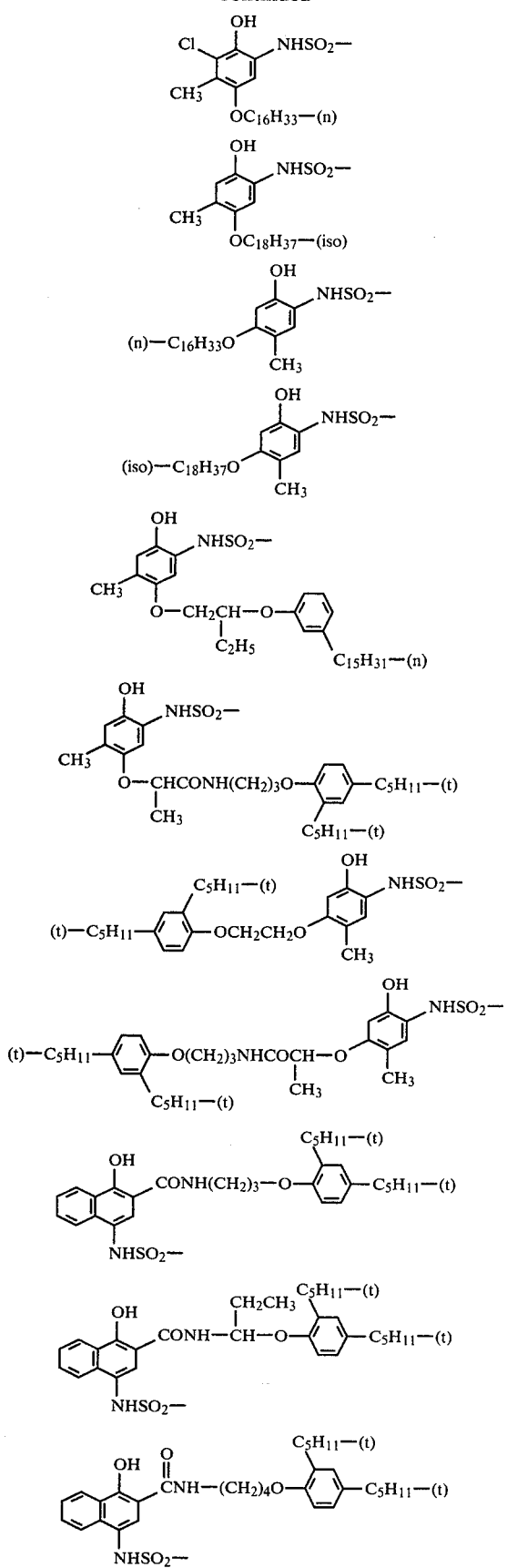
-continued
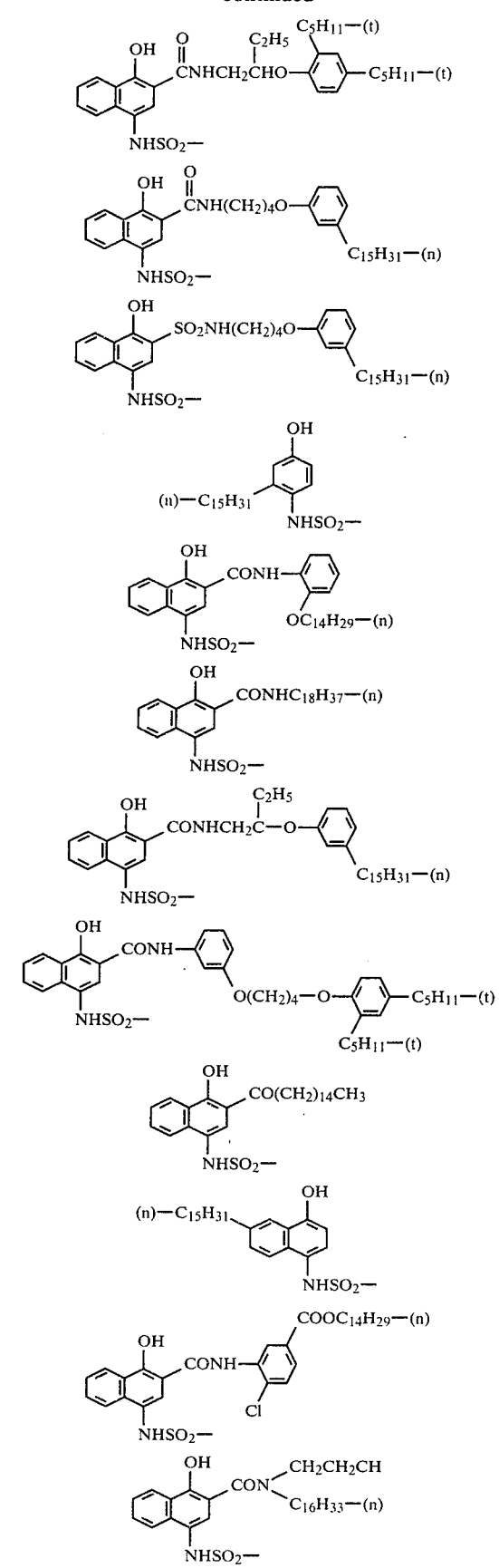

-continued

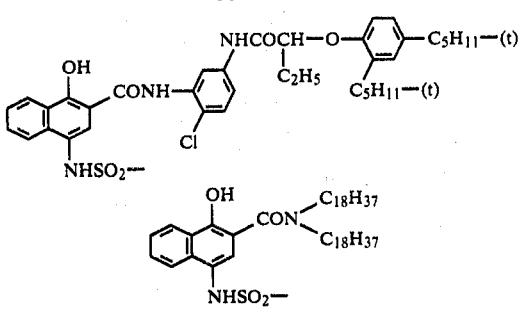

Furthermore, the groups described in *Research Disclosure*, Vol. 130, No. 13024 (February, 1975) and U.S. Pat. No. 4,053,312 are useful for Y.

A preferred compound according to the present invention is a compound having a dye moiety D represented by the formula (III), and in which $R^1$ represents a —CH$_2$CH$_2$— group;

$R^2$ represents a straight chain or branched chain alkyl group having 1 to 4 carbon atoms (for example, a methyl group, an ethyl group, a propyl group, an isopropyl group, a butyl group, etc.);

$Q^1$, which is present at the 2-position with respect to the hydroxy group of the naphthalene ring, represents a hydrogen atom or a sulfamoyl group represented by the formula —SO$_2$NR$^3$R$^4$, wherein R$^3$ and R$^4$, which may be the same or different, each represents an unsubstituted alkyl group having 1 to 4 carbon atoms or a substituted alkyl group having 1 to 4 carbon atoms in the alkyl moiety, with examples of suitable substituents for the substituted alkyl group for R$^3$ and R$^4$ including a cyano group, an alkoxy group, a hydroxy group, a carboxy group, a sulfo group, etc., and also R$^3$ and R$^4$ can combine directly or through an oxygen atom to form a 5- or 6-membered ring;

$X^1$ and $X^2$ each represents an —SO$_2$— group;

Ar represents an m- or p-phenylene group;

Y represents a sulfamoyl group represented by the general formula (VI);

$Z^1$ represents a chlorine atom, a fluorine atom, a bromine atom, a cyano group, a nitro group, a trifluoromethyl group, a fluorosulfonyl group, a sulfamoyl group represented by the formula —SO$_2$NHR$^{11}$, wherein R$^{11}$ represents, preferably, an unsubstituted alkyl group having 1 to 4 carbon atoms or a substituted alkyl group having 1 to 4 carbon atoms in the alkyl moiety, with examples of suitable substituents in the substituted alkyl group including a cyano group, an alkoxy group, a hydroxy group, a carboxy group, a sulfo group, etc., an unsubstituted alkylsulfonyl group having 1 to 4 carbon atoms, a substituted alkylsulfonyl group having 1 to 4 carbon atoms in the alkyl moiety (with examples of suitable substituents including a cyano group, an alkoxy group, a hydroxy group, a carboxy group, a sulfo group, etc.), an unsubstituted phenylsulfonyl group, or a substituted phenylsulfonyl group (with examples of suitable substituents including a hydroxy group, a halogen atom, a carboxy group, a sulfo group, a sulfamoyl group, etc.); and $Z^2$ represents a hydrogen atom, a chlorine atom, a bromine atom or a fluorine atom.

A particularly preferred compound according to the present invention is a compound having a dye moiety D represented by the formula (III), and in which $R^1$ represents a —CH$_2$CH$_2$— group;

$R^2$ represents a straight chain or branched chain alkyl group having 1 to 4 carbon atoms (e.g., a methyl group, an ethyl group, a propyl group, an isopropyl group, a butyl group, etc.);

$Q^1$ represents a hydrogen atom;

$X^1$ and $X^2$ each represents an —SO$_2$— group;

Ar represents an m-phenylene group;

Y represents a sulfamoyl group represented by the general formula (VI);

$Z^1$ represents a chlorine atom, a bromine atom, a cyano group, a trifluoromethyl group, a nitro group or an alkylsulfonyl group having 1 to 4 carbon atoms (e.g., a methylsulfonyl group, an ethylsulfonyl groups, etc.); and $Z^2$ represents a hydrogen atom, a chlorine atom or a bromine atom.

Another preferred compound according to the present invention is a compound having a dye moiety D represented by the formula (IV), and in which $R^1$ represents a —CH$_2$CH$_2$— group;

$R^2$ represents a straight chain or branched chain alkyl group having 1 to 4 carbon atoms (for example, a methyl group, an ethyl group, a propyl group, an isopropyl group, a butyl group, etc.);

$X^1$ represents an —SO$_2$— group;

$Q^1$ represents a hydrogen atom or a sulfamoyl group represented by the formula —SO$_2$NR$^3$R$^4$, wherein R$^3$ and R$^4$, which may be the same or different, each represents an unsubstituted alkyl group having 1 to 4 carbon atoms or a substituted alkyl group having 1 to 4 carbon atoms in the alkyl moiety, with examples of suitable substituents in the substituted alkyl group including a cyano group, an alkoxy group, a hydroxy group, a carboxy group, a sulfo group, etc., and also R$^3$ and R$^4$ can combine directly or through an oxygen atom to form a 5- or 6-membered ring;

$Q^2$ represents a hydroxy group or an —NHSO$_2$R$^4$ group, wherein R$^4$ has the same meaning as defined above, except that R$^4$ is not a hydrogen atom, at the 5-position;

$M^1$ represents a hydrogen atom, an unsubstituted alkyl group having 1 to 4 carbon atoms, an alkoxy group having 1 to 4 carbon atoms or a chlorine atom; and Y represents a sulfamoyl group represented by the general formula (VI).

Another particularly preferred compound according to the present invention is a compound having a dye moiety D represented by the formula (IV), and in which $R^1$ represents a —CH$_2$CH$_2$— group;

$R^2$ represents a straight chain or branched chain unsubstituted alkyl group having 1 to 4 carbon atoms (for example, a methyl group, an ethyl group, an n-propyl group, an isopropyl group, an n-butyl group, etc.);

$Q^1$ represents a group of the formula

—SO$_2$N (CH$_2$)$_4$;

$Q^2$ represents an —$NHSO_2$-alkyl group (with the alkyl group having 1 to 4 carbon atoms) at the 5-position;

$M^1$ represents a methyl group or a hydrogen atom; and

Y represents a sulfamoyl group represented by the general formula (VI).

A still further preferred compound according to the present invention is a compound having a dye moiety D represented by the formula (V), and in which $R^1$ represents a —$CH_2CH_2$— group;

$R^2$ represents a straight chain or branched chain unsubstituted alkyl group having 1 to 4 carbon atoms (for example, a methyl group, an ethyl group, an n-propyl group, an isopropyl group, an n-butyl group, etc.);

$X^1$ represents an —$SO_2$— group;

$M^1$ represents a hydrogen atom, an unsubstituted alkyl group having 1 to 4 carbon atoms, an alkoxy group having 1 to 4 carbon atoms or a halogen atom;

$M^2$ represents a hydrogen atom or an unsubstituted alkyl group having 1 to 4 carbon atoms;

$Q^3$ represents a cyano group or a —$CONR^3R^4$ group, wherein $R^3$ and $R^4$, which may be the same or different, each represents a hydrogen atom, an unsubstituted alkyl group having 1 to 4 carbon atoms or a substituted alkyl group having 1 to 4 carbon atoms in the alkyl moiety, with examples of suitable substituents in the substituted alkyl group including a cyano group, an alkoxy group, a hydroxy group, a carboxy group, a sulfo group, etc., and also $R^3$ and $R^4$ can combine directly or through an oxygen atom to form a 5- or 6-membered ring; and Y represents a sulfamoyl group represented by the general formula (VI).

Still another particularly preferred compound according to the present invention is a compound having a dye moiety D represented by the formula (V), and in which $R^1$ represents a —$CH_2CH_2$— group;

$R^2$ represents a straight chain or branched chain unsubstituted alkyl group having 1 to 4 carbon atoms (for example, a methyl group, an ethyl group, an n-propyl group, an isopropyl group, an n-butyl group, etc.);

$X^1$ represents an —$SO_2$— group;

$M^1$ represents a hydrogen atom, an unsubstituted alkyl group having 1 to 4 carbon atoms, an alkoxy group having 1 to 4 carbon atoms or a chlorine atom;

$M^2$ represents a hydrogen atom or an unsubstituted alkyl group having 1 to 4 carbon atoms;

$Q^3$ represents a cyano group; and

Y represents a sulfamoyl group represented by the general formula (VI).

Of the above-described compounds, compounds in which Y is present at the 3-position to the D—$SO_2NH$— group and the $R^2$—O—$R^1$—O— group is present at the 4-position to the D—$SO_2NH$— group are excellent from the standpoint of the photographic properties thereof and the preparation thereof.

That is, compounds in which the redox moiety represented by the general formula (I) is a group of the formula (XI):

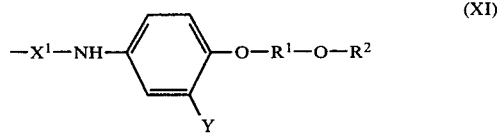

wherein $X^1$, $R^1$, $R^2$ and Y each has the same meaning as defined in the general formula (I), are excellent.

Furthermore, of the above-described compounds, compounds in which Y is an o-hydroxyphenylsulfamoyl group having a ballast group bonded thereto or a nucleus-substituted o-hydroxyphenylsulfamoyl group having a ballast group bonded thereto are excellent. Particularly, compounds in which Y is an o-hydroxyphenylsulfamoyl group having an alkyl group (having 7 or less carbon atoms, preferably 1 to 2 carbon atoms) at the meta position to the hydroxy group in addition to a ballast group are preferred. That is, compounds in which the redox moiety represented by the general formula (I) is a group of the formula (XII):

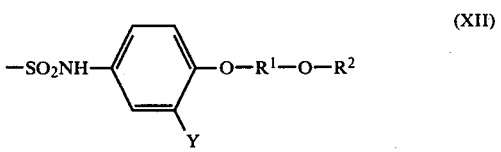

wherein $R^1$ has the same meaning as defined in the general formula (I); $R^2$ represents an alkyl group; Y represents an o-hydroxyphenylsulfamoyl group having an alkyl group at the meta position to the hydroxy group in addition to a ballast group are particularly preferred.

Specific examples of dye-releasing redox compounds according to the present invention are illustrated below. However, the present invention should not be construed as being limited to these specific examples.

Compound (1)

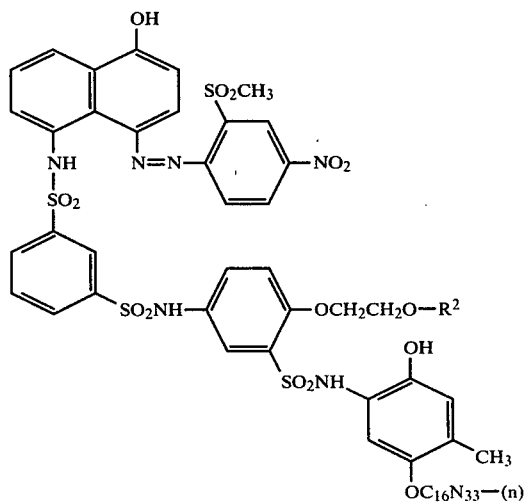

wherein $R^2$ is $CH_3$

Compound (2)

$R^2$ is $C_2H_5$ in the formula of Compound (1)

Compound (3)
R² is (n)-C₄H₉ in the formula of Compound (1)

Compound (4)
R² is (iso)-C₃H₇ in the formula of Compound (1)

Compound (5)
R² is (n)-C₃H₇ in the formula of Compound (1)

Compound (6)

[Structure: naphthalene with OH, SO₂CH₃, NH, N=N linked to phenyl-NO₂; SO₂-phenyl-SO₂NH-phenyl(OCH₂CH₂O-R²)-SO₂NH-phenyl with OH, CH₃, O-CH₂CH₂O-phenyl with two C₅H₁₁-(t) groups]

wherein R² is CH₃

Compound (7)
R² is C₂H₅ in the formula of Compound (6)

Compound (8)
R² is (n)-C₄H₉ in the formula of Compound (6)

Compound (9)
R² is (iso)-C₃H₇ in the formula of Compound (6)

Compound (10)
R² is (n)-C₃H₇ in the formula of Compound (6)

Compound (11)

[Structure: naphthalene with OH, SO₂CH₃, NH, N=N linked to phenyl-NO₂; SO₂-phenyl-SO₂NH-phenyl(OCH₂CH₂OR²)-SO₂NH-phenyl with OH, CH₃, O-C₁₈H₃₇-(n)]

wherein R² is CH₃

Compound (12)
R² is C₂H₅ in the formula of Compound (11)

Compound (13)
R² is (n)-C₄H₉ in the formula of Compound (11)

Compound (14)
R² is (iso)-C₃H₇ in the formula of Compound (11)

Compound (15)
R² is (n)-C₃H₇ in the formula of Compound (11)

Compound (16)

[Structure: naphthalene with OH, SO₂CH₃, NH, N=N linked to phenyl-NO₂; SO₂-phenyl-SO₂NH-phenyl(OCH₂CH₂OR²)-SO₂NH-phenyl with OH, CH₃, O-CH₂CO-NH(CH₂)₃O-phenyl with two C₅H₁₁-(t) groups]

wherein R² is CH₃

Compound (17)

R² is C₂H₅ in the formula of Compound (16)

Compound (18)

R² is (n)-C₄H₉ in the formula of Compound (16)

Compound (19)

R² is (iso)-C₃H₇ in the formula of Compound (16)

Compound (20)

R² is (n)-C₃H₇ in the formula of Compound (16)

Compound (21)

[Chemical structure]

Compound (22)

[Chemical structure]

Compound (23)

[Chemical structure]

wherein R² is CH₃

Compound (24)

R² is C₂H₅ in the formula of Compound (23)

Compound (25)

R² is (n)-C₄H₉ in the formula of Compound (23)

Compound (26)

R² is (iso)-C₃H₇ in the formula of Compound (23)

Compound (27)

R² is (n)-C₃H₇ in the formula of Compound (23)

Compound (28)

[Chemical structure]

Compound (29)
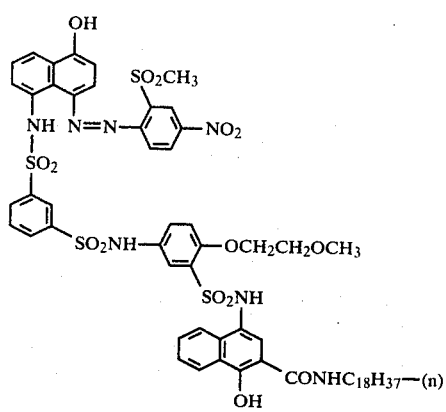
Compound (30)
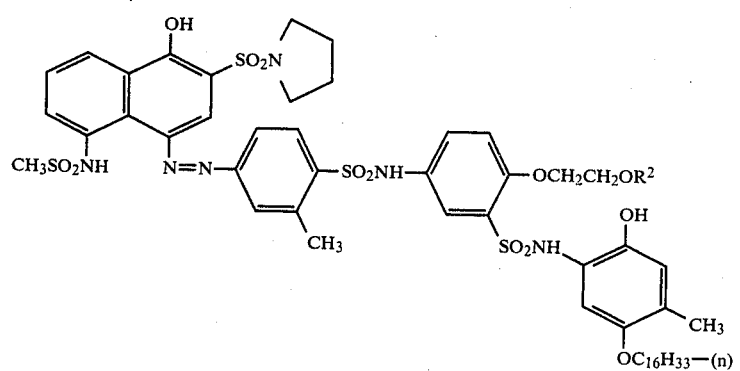
wherein $R^2$ is $CH_3$
Compound (31)
$R^2$ is $C_2H_5$ in the formula of Compound (30)
Compound (32)
$R^2$ is (n)-$C_4H_9$ in the formula of Compound (30)
Compound (33)
$R^2$ is (iso)-$C_3H_7$ in the formula of Compound (30)
Compound (34)
$R^2$ is (n)-$C_3H_7$ in the formula of Compound (30)
Compound (35)
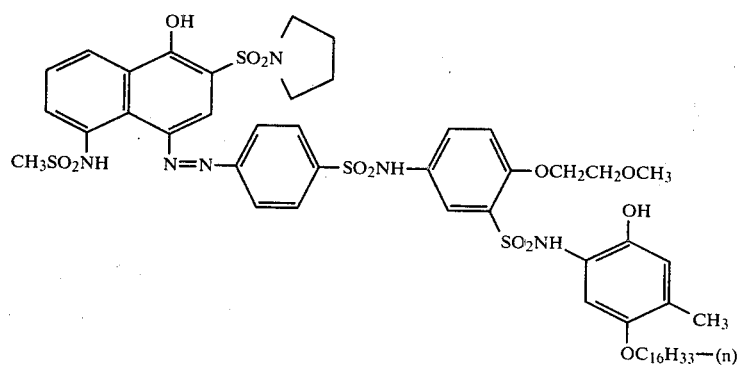

Compound (36)

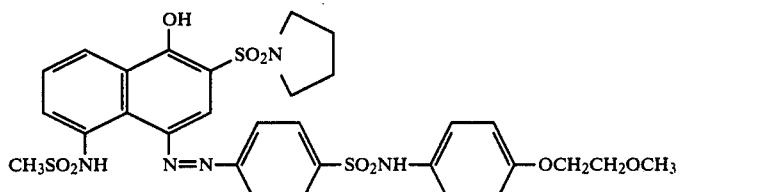

Compound (37)

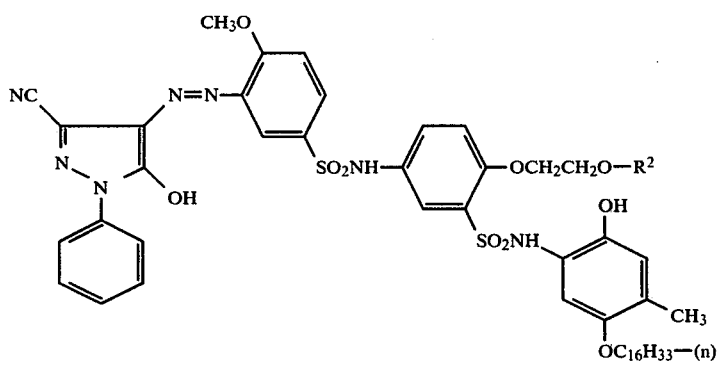

wherein $R^2$ is $CH_3$

Compound (38)

$R^2$ is $C_2H_5$ in the formula of Compound (37)

Compound (39)

$R^2$ is (n)-$C_4H_9$ in the formula of Compound (37)

Compound (40)

$R^2$ is (iso)-$C_3H_7$ in the formula of Compound (37)

Compound (41)

$R^2$ is (n)-$C_3H_7$ in the formula of Compound (37)

Compound (42)

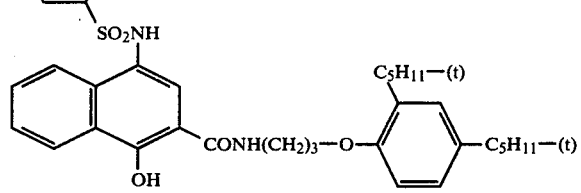

wherein $R^2$ is $CH_3$

Compound (43)

$R^2$ is $C_2H_5$ in the formula of Compound (42)

Compound (44)

$R^2$ is (n)-$C_4H_9$ in the formula of Compound (42)

Compound (45)

$R^2$ is (iso)-$C_3H_7$ in the formula of Compound (42)

Compound (46)

$R^2$ is (n)-$C_3H_7$ in the formula of Compound (42)

Compound (47)

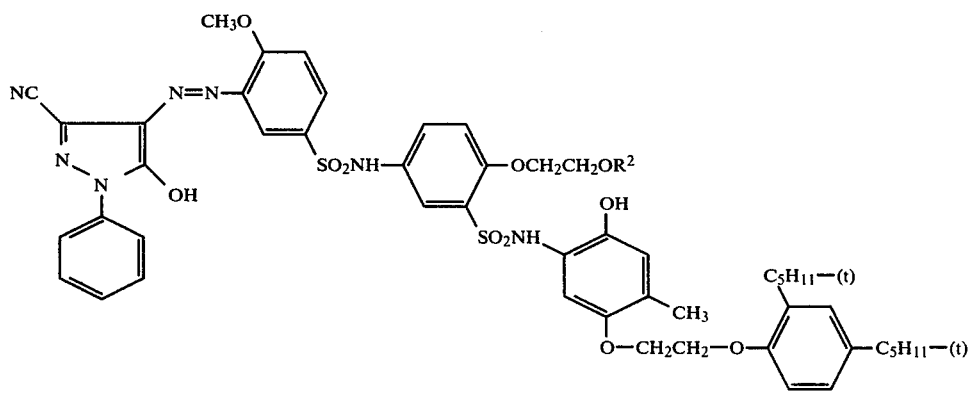

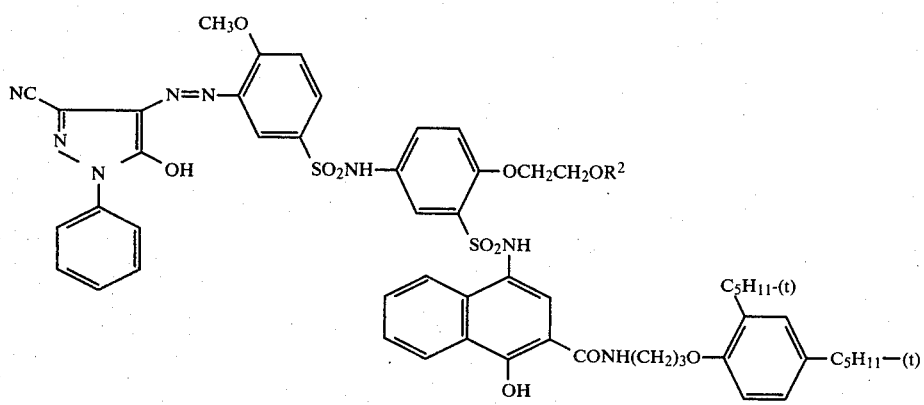

wherein R² is CH₃

Compound (48)

R² is C₂H₅ in the formula of Compound (47)

Compound (49)

R² is (n)-C₄H₉ in the formula of Compound (47)

Compound (50)

R² is (iso)-C₃H₇ in the formula of Compound (47)

Compound (51)

R² is (n)-C₃H₇ in the formula of Compound (47)

Compound (52)

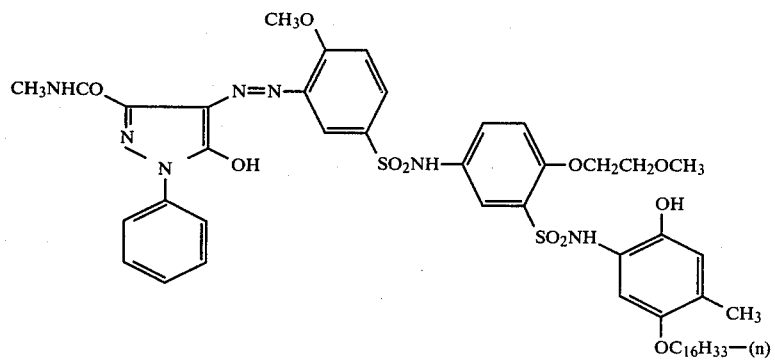

Compound (53)

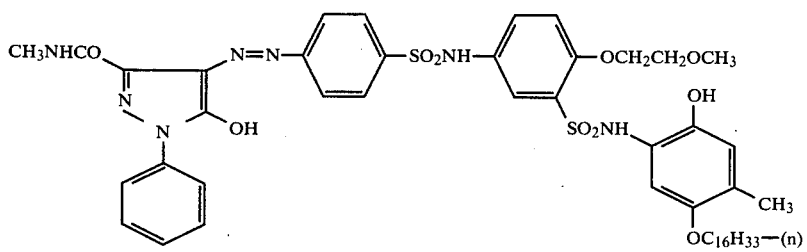

The dye-releasing redox compound according to the present invention releases a novel dye compound represented by the following formula (XIII):

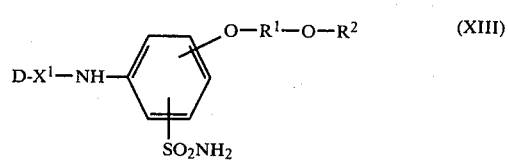

wherein $R^1$, $R^2$, $X^1$ and D each has the same meaning as defined in the general formula (I), when the compound is oxidized under alkaline conditions.

With respect to the dye compounds released from the above-described specific examples of redox compounds, cyan dye compounds are released from Compounds (1) to (29), magenta dye compounds are released from Compounds (30) to (36) and yellow dye compounds are released from Compounds (37) to (53). The term "dye compound" means a compound having a dye moiety (D) and a moiety split from the redox moiety, as shown by the formula (XIII).

The dye-releasing redox compound according to the present invention can be obtained by a condensation reaction of a sulfonyl halide or a carboxylic acid halide represented by the formula (XIVa):

D-X¹-X³   (XIVa)

with an amine represented by the formula (XIVb):

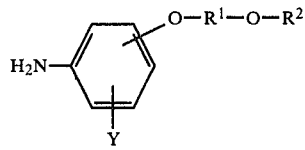

wherein in the formulas (XIVa) and (XIVb) D, $X^1$, $R^1$, $R^2$ and Y each has the same meaning as defined in the formula (I); and $X^3$ represents a halogen atom (for example, a chlorine atom, a fluorine atom, etc.).

In general, the condensation reaction is preferably carried out in the presence of a basic compound. Examples of suitable basic compounds which can be employed include a hydroxide of an alkali metal or an alkaline earth metal (for example, sodium hydroxide, potassium hydroxide, barium hydroxide, calcium hydroxide, etc.), an aliphatic amine (for example, triethylamine, etc.), an aromatic amine (for example, N,N-diethylamine, etc.), a heteroaromatic amine (for example, pyridine, quinoline, α-, β- or γ-picoline, lutidine, collidine, 4-(N,N-dimethylamino)pyridine, etc.), or a heterocyclic base (for example, 1,5-diazabicyclo[4,3,0]nonene-5, 1,8-diazabicyclo[5,4,0]undecene-7, etc.). A heteroaromatic amine is particularly preferred of the above-described basic compounds where a compound represented by the formula (XIVa) wherein $X^3$ is a chlorine atom and $X^1$ is an —SO₂— group, that is, a sulfonyl chloride is used. The molar ratio of the compound of the formula (XIV$_a$) to the compound of the formula (XIV$_b$) is preferably about 1:1, The molar ratio of the basic compound to the compound of the formula (XIVa) can be about 1:1 to about 100:1, preferably 1:1 to 20:1, more preferably 1:1 to 10:1. Suitable reaction media which can be used include a wide variety of solvents such as carboxylic amide solvents (e.g., N,N-dimethylacetamide, N,N-dimethylformamide, etc.), ethereal solvents, (e.g., tetrahydrofuran, dioxane, 1,2-dimethoxyethane, diglyme (diethylene glycol dimethyl ether), etc.), ketonic solvents (e.g., acetone, methyl ethyl ketone, etc.), ester solvents (e.g., ethyl acetate, 2-methoxyethyl acetate, etc.), sulfoxide solvents (e.g., dimethyl sulfoxide), phosphoric amide solvents (e.g., hexamethylphosphoric triamide, etc.) and nitride solvents (e.g., acetonitrile, etc.). They can be selected depending upon the solubility of the starting materials and the products. The condensation reaction can be carried out at about −30° to about 150° C., more preferably −10° to 100° C., still more preferably 0° C. to 50° C. The reaction time depends upon the basic compound as described above, the reaction solvent used, the reaction temperature employed, etc. The condensation reaction is generally accomplished within about 5 hours, but longer stirring or agitation may be preferred depending on the reaction conditions used.

The sulfonyl halide represented by the formula (XIVa) wherein $X^1$ is an —SO₂— group can be obtained by halogenation of the corresponding sulfonic acid or a salt thereof. Particularly, a compound in which $X^3$ is a chlorine atom is excellent since it has a good reactivity and it is easily prepared.

Examples of sulfonyl halides represented by the formula (XIVa) are described, for example, in U.S. Pat. Nos. 3,928,312, 4,013,633, 3,929,760, 3,954,476, 3,931,144, 3,942,987, 3,932,380 and 4,013,635, etc.

A typical method for the preparation of the amine represented by the formula (XIVb) is schematically illustrated below:

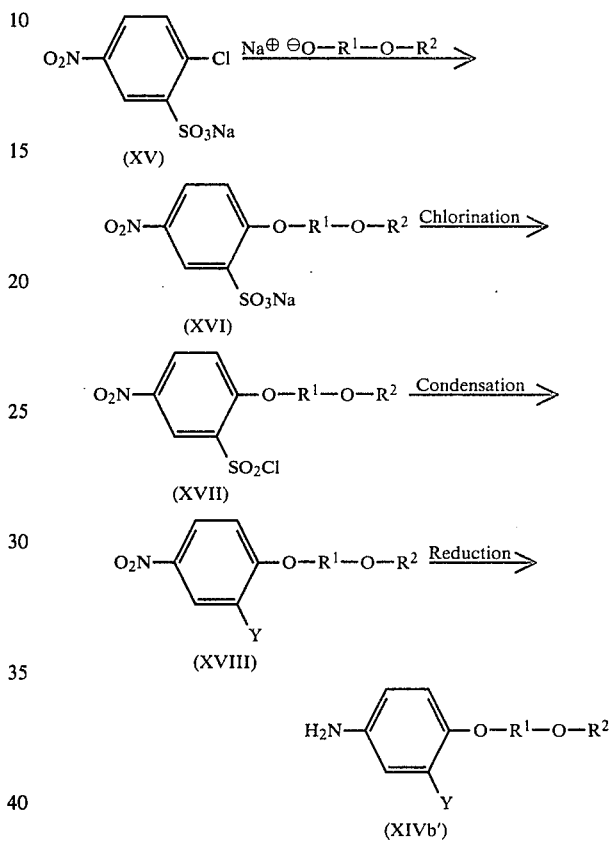

wherein $R^1$, $R^2$ and Y each has the same meaning as defined in the formula (I).

The first step is a reaction of a compound of the formula (XV) with an $R^2$—O—$R^1$—O⁻ moiety and the latter moiety is obtained by treating an alcohol of the formula $R^2$—O—$R^1$—OH with metallic sodium or sodium hydride. The reaction for obtaining a compound of the formula (XVI) is preferably carried out using an excess amount of the alcohol of the formula $R^2$—O—$R^1$—OH as a solvent.

Another method for obtaining a compound of the formula (XVI) is to suspend a compound of the formula (XV) in an alcohol of the formula $R^2$—O—$R^1$—OH which is used as a solvent, and to react with sodium hydroxide in the presence of manganese dioxide or sodium silicate (Na₂O.n'SiO₂ wherein n' is about 1 to about 3). This method is preferred since an inflammable material such as metallic sodium or sodium hydride is not used.

In order to convert the compound of the formula (XVI) to a compound of the formula (XVII), a chlorinating agent such as phosphorus oxychloride (POCl₃), thionyl chloride (SOCl₂) or phosphorus pentachloride (PCl₅) is preferably used. The chlorination reaction is preferably carried out in the presence of N,N-dimethylacetamide, N,N-dimethylformamide, N-methylpyrrolidone, etc.

The condensation reaction of the sulfonyl chloride represented by the formula (XVII) and an o- or p-hydroxyarylamine having a ballast group bonded thereto to obtain a compound of the formula (XVIII) is preferably carried out in the presence of a basic compound, with suitable examples of basic compounds being as described with respect to the reaction of the compound of the formula (XIVa) with the compound of the formula (XIVb).

Typical examples of reduction reactions for obtaining a compound of the formula (XIVb') include a catalytic hydrogenation (e.g., using Raney nickel, palladium-carbon or charcoal as a catalyst), a reduction with iron powder, a reduction with hydrazine, etc. It should be emphasized that, in the compound of the formula (XIVb'), the basicity of the amino group is increased due to the presence of the $R^2-O-R^1-O-$ group. Accordingly, the following condensation reaction of the compound of the formula (XIVb') with a sulfonyl chloride of the formula (XIVa) proceeds easily. It is understood that using potassium 3-nitro-4-chlorobenzenesulfonate instead of the compound of the formula (XV) in the above-described processes, a compound having the substituent at a different position can be obtained.

Typical synthesis examples of the dye-releasing redox compounds used in the present invention and intermediates therefor are illustrated in detail below. Unless otherwise indicated herein, all parts, percents, ratios and the like are by weight.

SYNTHESIS EXAMPLE 1

Synthesis of Sodium 2-(2-Methoxyethoxy)-5-nitrobenzenesulfonate

[Method 1]

To a solution of sodium 2-methoxyethylate prepared by adding 7.3 g of sodium hydride (14.6 g of a 50% suspension in liquid paraffin) to 300 ml of methyl Cellosolve, was added 55 g of sodium 2-chloro-5-nitrobenzenesulfonate with stirring. The reaction mixture was heated at 80° to 85° C. on a water bath with stirring for 30 minutes. After filtering the mixture while hot, 1.5 liters of isopropyl alcohol was added to the filtrate. The crystals thus-precipitated were recovered by filtration and washed with 100 ml of isopropyl alcohol. Yield: 59 g; Melting Point: 238° to 239° C.

[Method 2]

A mixture of 5.2 g of sodium 2-chloro-5-nitrobenzenesulfonate, 0.6 g of manganese dioxide, 15 ml of methyl Cellosolve, 1 ml of water and 0.95 g of sodium hydroxide was stirred at 75° C. for 40 minutes. After cooling to 25° C., the insoluble materials were removed by filtration and the filtrate was poured into 100 ml of isopropyl alcohol. The crystals thus-precipitated were recovered by filtration to obtain 4.8 g of sodium 2-(2-methoxyethoxy)-5-nitrobenzenesulfonate. Melting Point: 238° to 239° C.

[Method 3]

In the same manner as described in Method 2 above except that 0.8 g of sodium silicate (No. 3, $Na_2O.n'SiO_2$ wherein n' is about 3) was used in place of the manganese dioxide, 4.8 g of sodium 2-(2-methoxyethoxy)-5-nitrobenzenesulfonate was obtained. Similar results were obtained using $Na_2O.n'SiO_2$ wherein n' is about 1, about 2 and about 2.5, respectively.

SYNTHESIS EXAMPLE 2

Synthesis of Sodium 2-(2-Ethoxyethoxy)-5-nitrobenzenesulfonate

To a solution of sodium 2-ethoxyethylate prepared by adding 7.3 g of sodium hydride (14.6 g of a 50% suspension in liquid paraffin) to 300 ml of ethyl Cellosolve, was added 55 g of sodium 2-chloro-5-nitrobenzenesulfonate. The reaction mixture was heated at 80° to 85° C. with stirring for 30 minutes. After completion of the reaction, the insoluble materials were removed by filtration and from the filtrate 150 ml of ethyl Cellosolve was distilled off under reduced pressure. To the concentrated solution was added 300 ml of isopropyl alcohol and the mixture was cooled with ice. The crystals thus-precipitated were recovered by filtration, washed with 100 ml of isopropyl alcohol and air-dried. Yield: 33 g; Melting Point: 248° to 249° C.

SYNTHESIS EXAMPLE 3

Synthesis of Sodium 2-(2-Butoxyethoxy)-5-nitrobenzenesulfonate

The title compound was obtained in the same manner as described in Method 2 of Synthesis Example 1 except that ethylene glycol monobutyl ether was used in place of the methyl Cellosolve. Melting Point: 104° to 106° C.

SYNTHESIS EXAMPLE 4

Synthesis of Compound (1)

(a) Synthesis of 2-(2-Methoxyethoxy)-5-nitrobenzenesulfonyl Chloride 59 g of sodium 2-(2-methoxyethoxy)-5-nitrobenzenesulfonate prepared as described in Synthesis Example 1 was added to a mixture of 200 ml of acetone and 75 ml of phosphorous oxychloride. 75 ml of N,N-dimethylacetamide was added dropwise to the mixture with stirring while the reaction mixture was maintained at 30° to 40° C. After completion of the addition, the mixture was allowed to stand with stirring until it cooled to room temperature (about 20°–25° C.). The reaction mixture was then poured into 600 ml of ice water, stirred for 30 minutes and the crystals thus-precipitated were collected by filtration. The crystals were washed with water and air-dried. Yield: 56 g; Melting Point: 74° to 74.5° C.

(b) Synthesis of 2-[2'-(2-Methoxyethoxy)-5'-nitrobenzenesulfonamido]-4-hexadecyloxy-5-methylphenol 20 g of 2-amino-4-hexadecyloxy-5-methylphenol hydrochloride and 18 g of 4-(2-methoxyethoxy)nitrobenzene-3-sulfonyl chloride prepared as described in Step (a) above were added to a mixture of 100 ml of tetrahydrofuran and 10 ml of pyridine and the mixture was stirred at room temperature for 3 hours. The reaction mixture was added to a mixture of 300 ml of ice water and 50 ml of a 35% hydrochloric acid aqueous solution with stirring. The crystals thus-precipitated were recovered with filtration, washed with water, air-dried and recrystallized from 100 ml of acetonitrile. Yield: 35 g; Melting Point: 85.5° to 86° C.

(c) Synthesis of 2-[2'-(2-Methoxyethoxy)-5'-aminobenzenesulfonamido]-4-hexadecyloxy-5-methylphenol 32 g of 2-[2'-(2-methoxyethoxy)-5'-nitrobenzenesulfonamido]-4-hexadecyloxy-5-methylphenol prepared as described in Step (b) above, 24 g of iron powder ($Fe_2O_3$), 12 g of $Fe_3O_4$, 0.6 g of ammonium chloride and 25 ml of water were added to 300 ml of isopropyl alcohol and the mixture was refluxed on a steam bath with stirring for 1 hour. After completion of the reaction, the mixture was filtered while hot and the filtrate was cooled with ice. The crystals thus-precipitated were recovered by filtration, washed with 50 ml of isopropyl alcohol and air-dried. Yield: 23 g; Melting Point: 142° to 144° C.

(d) Synthesis of 5-(3-Chlorosulfonylbenzenesulfonamido)-1-naphthol

To a stirred mixture of 2.1 g of 5-amino-1-naphthol (½ $H_2SO_4$ salt), 4.2 g of benzene-1,3-disulfonyl chloride, 10 ml of acetonitrile and 30 ml of methanol was added portionwise 3.4 g of sodium hydrogen carbonate at a temperature of 0° to 5° C. The mixture was stirred for 1 hour at 0° to 5° C. and poured into 300 ml of a 3% hydrochloric acid aqueous solution. The precipitated crude product was collected by filtration and recrystalized from benzene-ethyl acetate (1:1 by volume) to produce 2.9 g of the title compound.

(e) Synthesis of 4-(2-Methylsulfonyl-4-nitrophenylazo)-5-(3-chlorosulfonylbenzenesulfonamido)-1-naphthol 2-Methanesulfonyl-4-nitroaniline (50 m mol) was diazotized as described in J. B. Dickey, et al., *Ind. Eng. Chem.*, 45, 1730 (1953). The solution of the diazonium salt was added to the cooled methanolic solution (200 ml) of 20.0 g of 5-(3-chlorosulfonylbenzenesulfonamido)-1-naphthol prepared as described in Step (d) above. After stirring for 1 hour, the precipitated product was collected by filtration, washed successively with methanol and with water, dried in air at room temperature (20°–25° C.). Yield: 36.5 g. The product was used in Step (f) below without further purification.

(f) Synthesis of Compound (1)

11 g of 2-[2'-(2-methoxyethoxy)-5'-aminobenzenesulfonamido]-4-hexadecyloxy-5-methylphenol prepared as described in Step (c) above and 12 g of 4-(2-methylsulfonyl-4-nitrophenylazo)-5-(3-chlorosulfonylbenzenesulfonamido)-1-naphthol prepared as described in Step (e) above were added to 80 ml of N,N-dimethylacetamide at 0° to 5° C. and 15 ml of pyridine was added thereto. The reaction solution was maintained at 0° to 5° C. and stirred for 2 hours. After completion of the reaction, the reaction mixture was added to a mixture of 350 ml of ice water and 50 ml of a 35% hydrochloric acid aqueous solution. The crystals thus-precipitated were recovered by filtration, washed with 500 ml of water and air-dried. The crystals were treated with activated carbon and recrystallized from isopropyl alcohol. Yield: 12 g; Melting Point: 130° to 134° C.; λ max in methyl Cellosolve containing 2% of a 0.1 N sodium hydroxide aqueous solution: 634 nm ($\epsilon = 9.52 \times 10^4$)

SYNTHESIS EXAMPLE 5

Synthesis of Compound (30)

5.5 g of 2-[2'-(2-methoxyethoxy)-5'-aminobenzenesulfonamido]-4-hexadecyloxy-5-methylphenol prepared as described in Step (b) of Synthesis Example 4 and 5.4 g of 4-(4'-chlorosulfonyl-3'-methylphenylazo)-5-methylsulfonyl-2-pyrrolidinosulfonyl-1-naphthol were dissolved in N,N-dimethylacetamide. To the solution, 2.3 ml of pyridine was added dropwise and the mixture was stirred at room temperature for 1.5 hours. The mixture was then poured into a 3% hydrochloric acid aqueous solution and the solids thus-precipitated were recovered by filtration. 5 g of Compound (30) was obtained after recrystallization from methyl Cellosolve acetate. Melting Point: 168° to 173° C. The 4-(4'-chlorosulfonyl-3'-methylphenylazo)-5-methylsulfonyl-2-pyrrolidinosulfonyl-1-naphthol used was obtained by reacting 5-bis(methanesulfonyl)-amino-1-methanesulfonyloxy-2-naphthalenesulfonyl chloride (as disclosed in U.S. Pat. No. 3,954,476) and pyrrolidine, coupling the resulting product with diazotized 4-amino-2-methylbenzenesulfonic acid, and converting the sulfonic acid group of the resulting dye to a sulfonyl chloride group.

SYNTHESIS EXAMPLE 6

Synthesis of Compound (37)

17.8 g of 2-[2'-(2-methoxyethoxy)-5'-aminobenzenesulfonamido]-4-hexadecyloxy-5-methylphenol prepared as described in Step (b) of Synthesis Example 4 and 12.5 g of 1-phenyl-3-cyano-4-[5'-chlorosulfonyl-2'-methoxyphenylazo]-5-pyrazolone (as described in U.S. Pat. No. 4,013,633) were dissolved in 60 ml of N,N-dimethylacetamide. To the solution, 4.8 ml of pyridine was added dropwise (at 7° C.; over a 10 minute period), and the mixture was stirred at room temperature for 1 hour and 45 minutes. Then a mixture of 60 ml of methanol and 20 ml of water was added to the reaction mixture and the crystals thus-precipitated were recovered by filtration. After recrystallization three times from acetonitrile, 25.3 g of Compound (37) was obtained. Melting Point: 142° to 145° C.

In the reproduction of natural color by subtractive color photography, a color photographic element comprising at least two combinations of each of a silver halide emulsion having a selective spectral sensitivity in a certain wavelength region and a compound capable of providing a dye having a selective spectral absorption at the same wavelength region as the silver halide is used. In particular, a color photographic element comprising a support having coated thereon a combination of a blue-sensitive silver halide emulsion and a compound capable of providing a yellow dye, a combination of a green-sensitive silver halide emulsion and a compound capable of providing a magenta dye, and a combination of a red-sensitive silver halide emulsion and a compound capable of providing a cyan dye is useful. As a matter of course, diffusible dye-releasing redox compounds of this invention can be used as the compounds capable of providing the above-described dyes. These combinations of units of the silver halide emulsions and the dye providing compounds may be coated on a support as layers in a face-to-face relationship or may be coated on a support as a layer containing a mixture of particles of the silver halides and the dye providing compounds.

In a preferred multilayer structure, a blue-sensitive silver halide emulsion layer, a green sensitive silver halide emulsion layer and a red-sensitive silver halide emulsion layer are positioned in this order from the side of incident light of exposure and, in particular, it is desirable for a yellow filter layer to be positioned between the blue-sensitive silver halide emulsion layer and the green-sensitive silver halide emulsion layer when a highly sensitive silver halide emulsion containing silver iodide is used. Tye yellow filter layer usually contains a dispersion of yellow colloidal silver, a dispersion of an oil-soluble yellow dye, an acid dye mordanted to a basic polymer, or a basic dye mordanted to an acid polymer.

It is advantageous for the silver halide emulsion layers to be separated from each other by an interlayer. The interlayer acts to prevent the occurrence of undesirable interactions between the differently color-sensitized silver halide emulsion layers. The interlayer employed in such a case is usually composed of a hydrophilic polymer such as gelatin, polyacrylamide, a partially hydrolyzed product of polyvinyl acetate, etc., a polymer containing fine pores formed from a latex of a hydrophilic polymer and a hydrophobic polymer, e.g., as described in U.S. Pat. No. 3,625,685, or a polymer whose hydrophilic property is gradually increased by the liquid processing composition, such as calcium alginate, as described in U.S. Pat. No. 3,384,483, individually or as a combination thereof.

The silver halide emulsions which can be used in this invention are a dispersion of silver chloride, silver bromide, silver chlorobromide, silver iodobromide, silver chloroiodobromide or a mixture thereof in a hydrophilic colloid. The halide composition of the silver halide is selected depending on the purpose of using the color photographic materials and the processing conditions for the color photographic materials, but a silver bromide emulsion, a silver iodobromide emulsion or a silver chloriodobromide emulsion having a halide composition of less than about 10 mol% iodide, less than about 30 mol% chloride, and the rest bromide is particularly preferred. The grain size of the silver halide used may be a conventional grain size or a fine grain size but silver halides having a mean grain size of from about 0.1 micron to about 2 microns are preferred. Furthermore, depending on the specific purpose of using the color photographic materials, it is sometimes desirable to use a silver halide having a uniform grain size. The silver halide grains used in this invention may have the form of a cubic system, an octahedral system, or mixed crystal system thereof. These silver halide emulsions may be prepared using conventional methods as described in, for example, P. Glafkides, *Chimie Photographique*, Chapters 18–23, 2nd Edition, Paul Montel, Paris (1957).

The silver halide emulsions used in the present invention are preferably chemically sensitized, e.g., by heating using the natural sensitizers contained in gelatin, a sulfur sensitizer such as sodium thiosulfate or N,N,N'-trimethylthiourea, a gold sensitizer such as a thiocyanate complex salt or thiosulfate complex salt of monovalent gold, or a reducing sensitizer such as stannous chloride or hexamethylenetetramine. Also, silver halide emulsions which form a latent image on the surface of the silver halide grains, silver halide emulsions which form a latent image inside the silver halide grains as described in U.S. Pat. Nos. 2,592,550, 3,206,313, etc., and direct positive silver halide emulsions can be used in the present invention.

Among these silver halide emulsions internal latent image forming type silver halide emulsions, i.e., those containing silver halide grains which have sensitivity centers mainly inside the silver halide grains where upon exposure a latent image is formed selectively while on the surface of which a latent image is formed to a lesser extent are preferred. These internal latent image forming type silver halide emulsions are characterized by the feature that the amount of silver obtained by development with surface developing agents after exposure (corresponding to surface latent image) is apparently smaller than the amount of silver obtained by development with internal developing agents (corresponding to total latent image) as described in T. H. James "The Theory of Photographic Process", 4th Ed. pages 171–176, Macmillan Co., New York (1977).

The internal latent image forming type silver halide emulsions can be prepared by various processes. Suitable examples thereof include Burton emulsions which are prepared by ammonium method and contain iodine in high amounts as described in E. J. Wall: Photographic Emulsions, pp 35–36 and 52–53, American Photographic Publishing Co. (1929) and U.S. Pat. Nos. 2,497,875 and 2,563,785, primitive emulsions which are prepared by ammonium method and contain large grains of small iodine amounts as described in German Patent Application (OLS) No. 2,728,108, silver halide emulsions prepared by abruptly decreasing the ammonium concentration of silver halide ammonium complex salt solution to precipitate silver halide grains as described in U.S. Pat. No. 3,511,662, conversion emulsions prepared by forming silver halide grains of a high solubility such as silver chloride and then converting them into silver halide of a low solubility such as silver (iodo)bromide using catastrophy precipitation method as described in U.S. Pat. No. 2,592,250, core shell emulsions prepared by mixing a chemically sensitized core emulsion of a large particle size with an emulsion of a small particle size followed by ripening to coat core grains with a shell of silver halide as described in U.S. Pat. No. 3,206,313 and British Pat. No. 1,011,062, core shell emulsions prepared by adding a soluble silver salt solution and a soluble halide solution simultaneously to a chemically sensitized monodispersed core emulsion while maintaining the concentration of silver at a constant level to coat the core grains with a shell of silver halide as described in U.S. Pat. No. 3,761,276 and British Pat. No. 1,027,146, halogen localized emulsions which contain emulsified grains having two layers having different halogen compositions as described in U.S. Pat. No. 3,935,014, emulsions incorporating another metal prepared by forming silver halide grains in an acidic medium containing trivalent metallic ions as described in U.S. Pat. No. 3,447,927, etc.

The silver halide emulsions used in the present invention may be stabilized with additives such as 4-hydroxy-6-methyl-1,3,3a,7-tetrazaindene, 5-nitroimidazole, 1-phenyl-5-mercaptotetrazole, 8-chloromercuriquinoline, benzenesulfinic acid, pyrocatechin, 4-methyl-3-sulfoethylthiazolidin-2-thione, 4-phenyl-3-sulfoethylthiazolidin-2-thione, etc., if desired. In addition, inorganic compounds such as cadmium salts, mercury salts, complex salts of platinum group metals such as the chloro complex salt of palladium, and the like are also useful for stabilizing the light-sensitive material of the present invention. Furthermore, the silver halide emulsions used in the present invention may contain sensitizing compounds such as a polyethylene oxide compound.

The silver halide emulsions used in the present invention can possess, if desired, a color sensitivity expanded with a spectral sensitizing dye or dyes. Examples of useful spectral sensitizers are cyanine, merocyanine, holopolar cyanine, styryl, hemicyanine, oxanole, hemioxanole, etc., dyes. Specific examples of suitable spectral sensitizers which can be used in this invention are described in, for example, P. Glafkides, supra. Chapters 35–41, and F. M. Hamer, *The Cyanine Dyes and Related Compounds*, Interscience. A particularly useful spectral sensitizer is a cyanine of which the nitrogen atom of the basic heterocyclic nucleus has been substituted with an aliphatic group (e.g., an alkyl group) having a hydroxy group, a carboxy group, or a sulfo group as described in, for example, U.S. Pat. Nos. 2,503,776, 3,459,553 and 3,177,210.

The dye-releasing redox compound used in this invention can be dispersed in a hydrophilic colloid using various techniques, depending on the type of dye-releasing redox compound. For example, when the dye-releasing redox compound has a dissociable group such as a sulfo group or a carboxy group, the dye-releasing redox compound can be added to an aqueous solution of a hydrophilic colloid as a solution in water or as an aqueous alkaline solution thereof. On the other hand, when the dye-releasing redox compound is sparingly soluble in aqueous medium but is readily soluble in organic solvents, the dye-releasing redox compound is first dissolved in an organic solvent and then the solution is finely dispersed in an aqueous solution of a hydrophilic colloid with stirring. Such a dispersing method is described in detail in, for example, U.S. Pat. Nos. 2,322,027, 2,801,171, 2,949,360 and 3,396,027.

To stabilize the dispersion of the dye-releasing redox compound and also to promote dye image formation, it is advantageous to incorporate the dye-releasing redox compound into an aqueous hydrophilic colloid solution as a solution in a solvent which is substantially insoluble in water and has a boiling point of higher than about 200° C. at normal pressure. Examples of suitable high boiling solvents which can be used for this purpose are aliphatic esters such as the triglycerides of higher fatty acids, dioctyl adipate, etc.; phthalic acid esters such as di-n-butyl phthalate, etc.; phosphoric acid esters such as tri-o-cresyl phosphate, tri-n-hexyl phosphate, tricyclohexyl phosphate, etc.; amides such as N,N-dimethyllaurylamide, etc.; and hydroxy compounds such as 2,4-di-n-amylphenol. Furthermore, to stabilize the dye-releasing redox compound and to promote dye image formation, it is also advantageous to incorporate an oleophilic polymer into the photosensitive layer together with the dye-releasing redox compound. Examples of suitable oleophilic polymers which can be used for this purpose are shellac, a phenol-formaldehyde condensate, poly-n-butyl acrylate, a copolymer of n-butyl acrylate and acrylic acid, an interpolymer of n-butyl acrylate, styrene, and methacrylamide, etc.

Such an oleophilic polymer may be dissolved in an organic solvent together with the dye-releasing redox compound and then may be dispersed in a photographic hydrophilic colloid such as gelatin as a solution thereof or may be added to a dispersion in a hydrophilic colloid of the dye-releasing redox compound as the hydrosol of a polymer prepared by emulsion polymerization, etc.

The dispersion of the dye-releasing redox compound can be greatly promoted by using a surface active agent as an emulsification aid. Examples of suitable surface active agents useful for dispersion of the dye-releasing redox compound used in this invention formaldehyde condensates having an average degree of condensation of 3.4 and having a p-nonylphenol sodium p-nonylphenoxybutylsulfonate ratio of 55:4 as described in Japanese Patent Application (OPI) No. 138726/78, sodium p-tert-octylphenyl polyoxyethylenesulfonate as described in U.S. Pat. No. 4,105,453, sodium triisopropylnaphthalenesulfonate, sodium dinonylnaphthalenesulfonate, sodium p-dodecylbenzenesulfonate, sodium dioctylsulfosuccinate, sodium cetylsulfate, and the anionic surface active agents as described in Japanese Patent Publication No. 4,295/64 and British Pat. No. 1,138,514. The use of these anionic surface active agents and the higher fatty acid ester of anhydrohexitol exhibits particularly excellent emulsifying capability as disclosed in U.S. Pat. No. 3,676,141. Furthermore, the dispersing methods disclosed in Japanese Patent Publication No. 13,837/68 and U.S. Pat. Nos. 2,992,104, 3,044,873, 3,061,428 and 3,832,173 can be effectively employed for dispersing the dye-releasing redox compounds used in this invention.

The light-sensitive element of the present invention is prepared by coating directly or indirectly at least one light-sensitive silver halide photographic emulsion layer with the dye-releasing redox compound according to the present invention associated therewith onto a substantially planar material which does not undergo large dimensional changes. Examples of suitable supports which can be used are cellulose acetate films, polystyrene films, polyethylene terephthalate films, polycarbonate films, etc., as are used as supports for conventional photographic materials. Other examples of suitable supports are papers and papers coated with a water-impermeable polymer such as polyethylene.

The methods described in U.S. Pat. Nos. 3,931,144, 3,928,312 and, Belgian Patent No. 788,268 can be employed as methods of forming diffusion transfer color photographic images by using dye-releasing redox compounds. These image forming methods can be effectively used with the dye-releasing redox compounds according to the present invention.

One embodiment of a series of steps for obtaining color diffusion transfer images using a dye-releasing redox compound according to the present invention is described below.

(A) A light-sensitive element comprising a support having thereon at least one light-sensitive silver halide emulsion layer with the dye-releasing redox compound according to the present invention associated therewith is image-wise exposed.

(B) An alkaline processing composition is spread on the above-described light-sensitive silver halide emulsion layer whereby development of all light-sensitive silver halide emulsion layers in the presence of a developing agent for silver halide is conducted.

(C) As a result, an oxidation product of the developing agent produced in proportion to the amount of exposure cross-oxidizes the dye-releasing redox compound.

(D) The above-described oxidation product of the dye-releasing redox compound splits to release a diffusible dye.

(E) The released diffusible dye image-wise diffuses to form a transferred image on an image-receiving layer (directly or indirectly) adjacent the light-sensitive silver halide emulsion layer.

In the above-described process, any silver halide developing agents which can cross-oxidize the dye-releasing redox compound can be used. These developing agents may be incorporated into the alkaline processing composition or may be incorporated into appropriate photographic layers of the light-sensitive element. Specific examples of suitable developing agents which can be used in this invention are, for example, black-and-white developing agents, e.g., hydroquinones such as methyl hydroquinone, t-butyl-hydroquinone; aminophenols such as N-methylaminophenol; pyrazolidones such as 1-phenyl-3-pyrazolidone, 1-phenyl-4,4-dimethyl-3-pyrazolidone, 1-phenyl-4-methyl-4-hydroxymethyl-3-pyrazolidone, 1-phenyl-4-methyl-3-pyrazolidone, 1-p-tolyl-4-hydroxymethyl-4-methyl-3-pyrazolidone; and color developing agents, e.g., phenylenediamines such as N,N-diethyl-p-phenylenediamine, 3-methyl-N,N-diethyl-p-phenylenediamine, 3-methoxy-N-ethoxy-p-phenylenediamine; etc.

Of the above-indicated developing agents, black-and-white developing agents having the capability, in general, of reducing the occurrence of stains in image-receiving layers are particularly preferred in comparison with color developing agents such as phenylenediamines.

Among the black-and white developing agents pyrazolidones are particularly preferred in using in combination with the dye-releasing redox compounds of the present invention.

In particular, it is advantageous to use 1-phenyl-3-pyrazolidone developing agents of the formula set out below in combination with the dye-releasing compounds of the present invention.

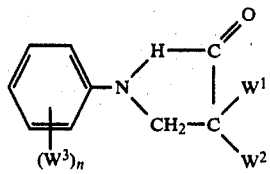

wherein $W^1$ and $W^2$, which may be the same or different, each represent a hydrogen atom, an unsubstituted alkyl group (e.g., a methyl group, an ethyl group, etc.) or a hydroxyalkyl group (e.g., a hydroxymethyl group, a hydroxyethyl group, etc.), $W^3$ represents a substituent group of which the sigma ($\sigma$) constant of Hammett is negative, and n is a positive integer of 1 to 5.

Examples of the suitable substituent groups for $W^3$ include an alkyl group (e.g., a methyl group, an ethyl group, etc.), an alkoxy group (e.g., a methoxy group, an ethoxy group, etc.), a hydroxy group, an amino group, an aryl group (e.g., a phenyl group, etc.), or the like group. When n is 2 suitable example of the substituent group for $W^3$ is a methyl group.

Of the above-indicated pyrazolidone compounds those having a half wave potential in polarography of about $-80$ mV to about $-200$ mV, preferably $-100$ mV to $-150$ mV (with respect to standard Caromel electrode, pH=11.0) are particularly useful since they can develop emulsified grains rapidly and at the same time undergo vigorous cross-oxidation thereby shortening time required to complete images.

When applying the dye-releasing redox compounds of the present invention to diffusion transfer method it is advantageous to use them in combination with the above-described hydroquinone compounds in addition to the afore-mentioned pyrazolidones in order to regulate the gradation of toe region.

In order to prevent the oxidation product of developing agent from being diffused into other color sensitive unit emulsion layers a compound capable of trapping such oxidation product (e.g., anti-color staining agent such as 2,5-di(sec-dodecyl)hydroquinone, 2,5-di(tert-pentadecyl)hydroquinone, etc.) can be added to each inter layer present between respective adjacent unit emulsion layers.

The dye-releasing redox compounds of the present invention can be used in such an amount that molar ratio of silver in the silver halide emulsion to be used in combination therewith to the dye-reducing redox comound is about 50 to 0.5:1 preferably 20 to 2:1.

When the dye-releasing redox compound according to this invention is used, the transferred image formed in the image-receiving layer is a negative image and the image remaining in the photosensitive layer is a positive image where a conventional surface latent image forming type emulsion is used without using a reversal mechanism. On the other hand, where a direct positive silver halide emulsion (including an emulsion which can provide a direct reversal positive image by fogging during development after exposure, for example, an internal latent image forming type silver halide emulsion or a solarization type silver halide emulsion) is employed as the silver halide emulsion in the above-described case, the transferred image formed in the image-receiving layer is a positive image.

Solarization type silver halide emulsions as described in C. E. K. Mees, *The Theory of the Photographic Process*, pages 261–297, Macmillan Co., New York (1942) can be used in this invention. These solarization type silver halide emulsions may be prepared using methods described in, for example, British Pat. Nos. 443,245 and 462,730 and U.S. Pat. Nos. 2,005,837, 2,541,472, 3,367,778, 3,501,305, 3,501,306 and 3,501,307.

Also, internal latent image forming type silver halide emulsions as described in, for example, U.S. Pat. No. 2,592,250, can be advantageously used in this invention. Typical examples of fogging agents which can be used for preparing this type of silver halide emulsion are the hydrazines described in U.S. Pat. Nos. 2,588,982 and 2,563,785, the hydrazide and hydrazone described in U.S. Pat. No. 3,227,552, and the quaternary salt compounds described in British Patent No. 1,283,835, Japanese Patent Publication No. 38,164/74, and U.S. Pat. Nos. 3,734,738, 3,719,494 and 3,615,615.

Furthermore, the diffusion inhibitor releasing (DIR) reversal silver halide emulsion system as described in U.S. Pat. Nos. 3,227,551, 3,227,554 and 3,364,022 or the reversal silver halide system using dissolution physical development as described in British Patent No. 904,364 can be employed in the case of using the dye-releasing redox compounds of this invention.

It is necessary for the image-receiving element used in this invention in combination with the above-described light-sensitive element to have an image-receiving mordanting layer comprising a mordant, such as the poly-4-vinylpyridine latex (in, preferably, polyvinyl alcohol) described in U.S. Pat. No. 3,148,061, the polyvinyl pyrrolidone described in U.S. Pat. No. 3,003,872, and the polymers containing quaternary ammonium salts as described in U.S. Pat. No. 3,239,337, individually or as a combination thereof. Also, the basic polymers as described in U.S. Pat. Nos. 2,882,156, 3,625,694 and 3,709,690 can be effectively used as the mordant for the image-receiving layer. Other examples of mordants which can be effectively used in this invention are described in U.S. Pat. Nos. 2,484,430, 3,271,147, 3,184,309, etc.

It is preferred for the light-sensitive film unit containing the light-sensitive element of this invention to be capable of neutralizing the alkali carried in from the alkaline processing composition. It is advantageous for this purpose for the light-sensitive film unit to include in a cover sheet or in an image-receiving element thereof a neutralizing layer containing an acid material in an amount sufficient to neutralize the alkali in the liquid processing composition, that is, containing an acid material at an area concentration higher than the equivalent of the alkali in the spread liquid processing composition. When a cover sheet having a neutralizing layer is used, the cover sheet can be superimposed on an image-receiving layer after such has been peeled from a light-sensitive element. Typical examples of preferred acid materials which can be used for this purpose are those described in U.S. Pat. Nos. 2,983,606, 2,584,030 and 3,362,819. The neutralizing layer may further contain a polymer such as cellulose nitrate, polyvinyl acetate, etc., and also the plasticizers as described in U.S. Pat. No. 3,557,237 in addition to the acid material. The acid material may be incorporated in the light-sensitive film unit in a microencapsulated form as described in German Patent Application (OLS) No. 2,038,254.

It is desirable for the neutralizing layer or the acid material-containing layer which can be used in this invention to be separated from the spread layer of the liquid processing composition by a neutralization rate controlling layer (or timing layer). Gelatin, polyvinyl alcohol, or the compounds described in U.S. Pat. Nos. 3,455,686, 4,009,030 and 3,785,815, Japanese Patent Application Nos. 77946/75 and 90616/75, Japanese Patent Application (OPI) Nos. 92022/73, 64435/74, 22935/74 and 77333/76, Japanese Patent Publication Nos. 15756/69, 12676/71 and 41214/73, German Patent Application (OLS) Nos. 1,622,936 and 2,162,227, *Research Disclosure*, No. 151, 15162 (1976), etc., can be effectively used as the timing layer. The timing layer acts to retard the reduction in the pH of the liquid processing composition by the neutralizing layer until the desired development and transfer of dyes can be sufficiently accomplished.

In a preferred embodiment of this invention, the image-receiving element has a multilayer structure comprising a support, a neutralizing layer, a timing layer, and a mordanting layer (or image-receiving layer) in this order. Image-receiving elements are described in detail in, for example, Japanese Patent Application (OPI) No. 13,285/72, U.S. Pat. No. 3,295,970 and British Patent No. 1,187,502.

The processing composition of the processing element used in this invention is a liquid composition containing the processing components necessary for developing silver halide emulsions and forming diffusion transfer dye images. The solvent of the processing composition is mainly water and contains, as the case may be, a hydrophilic solvent such as methanol, methyl Cellosolve, etc. The liquid processing composition contains an alkali in an amount sufficient to maintain the necessary pH on developing the silver halide emulsion layers and for neutralizing acids (e.g., hydrohalic acids such as hydrobromic acid, etc., and carboxylic acids such as acetic acid, etc.) formed during development and dye image formation. Examples of suitable alkalis are hydroxides or salts of ammonia, alkali metals or alkaline earth metals or amines, such as lithium hydroxide, sodium hydroxide, potassium hydroxide, an aqueous dispersion of calcium hydroxide, tetramethylammonium hydroxide, sodium carbonate, trisodium phosphate, diethylamine, etc. It is desirable for the liquid processing composition to contain an alkaline material in a concentration such that the pH thereof can be maintained at above about 10, in particular, above 12 at room temperature. Further preferably, the liquid processing composition contains a hydrophilic polymer such as high molecular weight polyvinyl alcohol, hydroxyethyl cellulose, sodium carboxymethyl cellulose, etc. These polymers contribute toward increasing the viscosity of the liquid processing composition above about 1 poise, preferably to 500 or 600 to 1,000 poises, at room temperature, which facilitates the uniform spreading of the processing composition at development as well as the formation of a non-fluid film when the aqueous medium has diffused into the photosensitive element and the image-receiving element during processing thereby concentrating the processing composition, which results in assisting unification of all of the elements after processing. The polymer film also contributes toward preventing coloring components from transferring into the image-receiving layer to stain the dye images formed after the formation of the diffusion transfer dye image is substantially completed.

As the case may be, it is advantageous for the liquid processing composition to further contain a light absorbing material such as $TiO_2$, carbon black, a pH indicating dye, etc., or the desensitizer as described in U.S. Pat. No. 3,579,333 for preventing the silver halide emulsion layers from being fogged by ambient light during processing outside the camera. Furthermore, the liquid processing composition used in this invention may contain a development inhibitor such as benzotriazole.

It is preferred for the above-described processing composition to be retained in a rupturable container as described in U.S. Pat. Nos. 2,543,181, 2,643,886, 2,653,732, 2,723,051, 3,056,491, 3,056,492, 3,152,515, etc.

The light-sensitive film unit of the present invention which has a construction such that after image-wise exposure, the processing of the film unit is performed by passing the film unit through a pair of juxtaposed pressure-applying members comprises:

(1) a support,
(2) a light-sensitive element as described above,
(3) an image-receiving element as described above,
(4) a processing element as described above, and
(5) a developing agent (which can be incorporated into the processing element or the light-sensitive element).

According to one embodiment of the film unit described above, the light-sensitive element and the image-receiving element are superimposed in a face-to-face relationship, and the unit is processed, after exposure, by spreading an alkaline processing composition between both elements. In this case, the image-receiving element may be stripped off after the transfer of the dye images has been completed or the dye images formed in the image-receiving layer may be observed without stripping the image-receiving element as described in U.S. Pat. No. 3,415,645.

In another embodiment of the film unit as described above, the image-receiving element and the light-sensitive element are positioned in this order in the film unit on a support. For example, a suitable photographic film unit is prepared by coating on a transparent support an image-receiving layer, a substantially opaque light reflecting layer (for example, a $TiO_2$-containing layer and a carbon black-containing layer) and a single or a plurality of light-sensitive layers as described above, in this order, as disclosed in Belgian Pat. No. 757,960. After exposing the light-sensitive element, the light-sensitive element is superimposed on an opaque cover sheet in a face-to-face relationship and then a liquid alkaline processing composition is spread between them.

Another embodiment of the superimposed and integral type film unit to which the present invention is most preferably applicable is disclosed in Belgian Pat. No. 757,959. According to this embodiment, the film unit is prepared by coating on a transparent support an image-receiving layer, a substantially opaque light reflective layer (as described above), and a single or a plurality of light-sensitive layers as described above, in this order, and further superimposing a transparent cover sheet on the light-sensitive layer in a face-to-face relationship. A rupturable container retaining an alkaline processing composition having incorporated therein a light-intercepting agent such as, for example, carbon black, is disposed adjacent to and between the uppermost layer of the above-described light-sensitive element and the transparent cover sheet. The film unit is image-wise exposed in a camera through the transparent cover sheet and then the rupturable container retaining the alkaline processing composition is ruptured by the pressure-applying members when the film unit is withdrawn from the camera to spread uniformly the processing composition containing the opacifying agent between the light-sensitive layer and the cover sheet, whereby the film unit is shielded from light and development proceeds.

In these embodiments of film units, the neutralization mechanism as described above is preferably incorporated therein. In particular, the neutralizing layer is preferably positioned in the cover sheet and, further, the timing layer is positioned on the side toward where the processing solution is to be spread, if desired.

Moreover, other useful embodiments of the integral type of film units wherein the dye-releasing redox compounds of this invention can be used are described in, for example, U.S. Pat. Nos. 3,415,644, 3,415,645, 3,415,646, 3,647,487, and 3,635,707 and German Patent Application (OLS) No. 2,426,980.

The present invention can provide advantageous effects and advantages and some of these are described below.

Firstly, color images having less light-fading are obtained because of the superiority in the light-fastness of the dyes released.

Secondly, color images with high quality are obtained when the dye-releasing redox compound according to the present invention is used together with other redox compounds of good hue, since the hue of the dyes released is excellent.

Thirdly, the amount of dyes remaining at exposed areas in light-sensitive elements is very small, since the transferability of the dye released is excellent. Therefore, it is effective to obtain negative color images composed of the unreacted dye-releasing redox compounds which are obtained by stripping off the light-sensitive element and subjecting it to bleach processing (i.e., the negative can be easily used).

The following examples are given to further illustrate this invention in greater detail.

EXAMPLE 1

On a transparent polyethylene terephthalate film support were coated the layers described below in the order listed to prepare an integral type of multilayer multicolor light-sensitive film unit.

(1) An image-receiving layer containing 3.0 g/m² of copoly[styrene-N-vinylbenzyldimethyl-p-chlorobenzylammonium chloride] and 3.0 g/m² of gelatin.

(2) A white reflecting layer containing 22 g/m² of titanium dioxide and 2.2 g/m² of gelatin.

(3) An opaque layer containing 2.7 g/m² of carbon black and 2.7 g/m² of gelatin.

(4) A layer containing 0.65 g/m² of Compound (1) of this invention (cyan dye-releasing redox compound) described above, 0.3 g/m² of N,N-diethyllaurylamide and 1.1 g/m² of gelatin.

(5) A layer containing a red-sensitive internal latent image type silver iodobromide emulsion (containing 2 mol% of silver iodide, 1.1 g/m² of gelatin and 1.4 g/m² of silver), 0.022 g/m² of 2-methyl-3-(2-formylethyl)benzothiazolium bromide and 0.06 g/m² of 2,5-di-tert-octylhydroquinone.

(6) A layer containing 1.8 g/m² of gelatin and 0.8 g/m² of 2,5-di-tert-octylhydroquinone.

(7) A layer containing 0.4 g/m² of gelatin.

(8) A layer containing 0.80 g/m² of a known magenta dye-releasing redox compound of the structural formula:

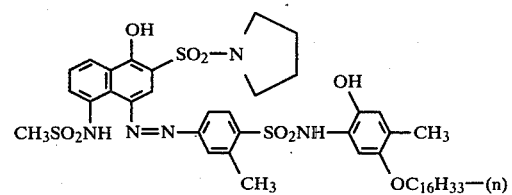

1.3 g/m² of N,N-diethyllaurylamide and 1.5 g/m² of gelatin.

(9) A layer containing a green-sensitive internal latent image type silver iodobromide emulsion (containing 2 mol% of silver iodide, 1.1 g/m² of gelatin and 1.4 g/m² of silver), 0.03 g/m² of 2,5-di-tert-octylhydroquinone and 0.019 g/m² of 2-methyl-3-(2-formylethyl)benzothiazolium bromide.

(10) A layer containing 1.5 g/m² of gelatin and 0.6 g/m² of 2,5-di-tert-octylhydroquinone.

(11) A layer containing 0.4 g/m² of gelatin.

(12) A layer containing 1.0 g/m² of a known yellow dye-releasing redox compound of the structural formula:

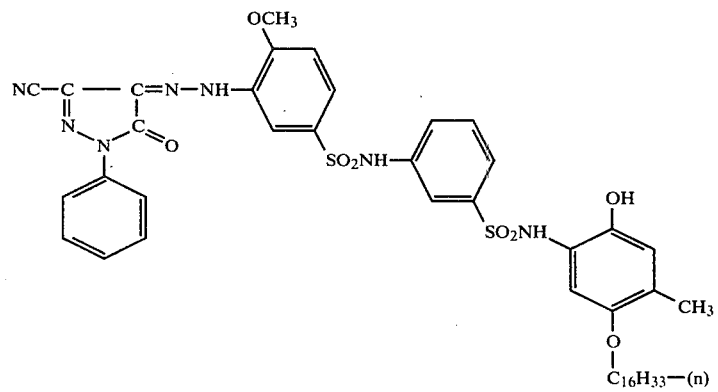

1.5 g/m² of N,N-diethyllaurylamide, 1.5 g/m² of gelatin and 0.01 g/m² of 2,5-di-tert-octylhydroquinone.

(13) A layer containing a blue-sensitive internal latent image type silver iodobromide emulsion (containing 2 mol% of silver iodide, 1.1 g/m² of gelatin and 1.4 g/m² of silver), 0.03 g/m² of 2,5-di-tert-octylhydroquinone and 0.017 g/m² of 2-methyl-3-(2-formylethyl)benzothiazolium bromide.

(14) A layer containing 0.6 g/m² of gelatin.

(15) A cover sheet produced by coating on a transparent polyethylene terephthalate film support the following layers in the order listed:

(i) A neutralizing layer composed of 10 g/m² of polyacrylic acid (ii) A timing layer composed of 10 g/m² of acetyl cellulose A sealed container retaining the processing solution having the composition described below:

| Composition of Viscous Processing Solution | |
| --- | --- |
| Water | 820 ml |
| Sulfuric Acid (1N aq. soln.) | 5 ml |
| Hydroxyethyl Cellulose | 60 g |
| 4-Hydroxymethyl-4-methyl-1-phenyl-3-pyrazolidone | 5 g |
| 5-Methylbenzotriazole | 2 g |
| tert-Butylhydroquinone | 0.4 g |
| Sodium Sulfite | 2 g |
| Carbon Black | 150 g |
| Sodium Hydroxide | 30 g | was assembled in the light-sensitive film unit. The container was so designed and disposed that a certain portion of the container was easily ruptured and the processing solution would be spread between the above-described layer (12) and the cover sheet (15) when the film unit was passed through a pair of juxtaposed pressure-applying rollers.

The above-described light-sensitive film unit was image-wise exposed in a camera and passed through a pair of rollers to spread the processing solution whereby transferred dye images were obtained. The cyan transferred image was particularly excellent of the transferred dye images from the standpoint of transferability and light fastness.

What is claimed is:

1. A photographic light-sensitive element for the color diffusion transfer process which comprises a support having thereon at least one light-sensitive silver halide emulsion layer with at least one of said silver halide emulsion layers having associated therewith a compound represented by the following general formula:

D-Redox Moiety wherein D represents an azo dye moiety represented by the following formula (IIa) or (IIb):

  (IIa)

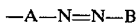  (IIb)

wherein A represents a coupling component residue derived from a phenol or a nucleus-substituted phenol, a 1- or 2-naphthol or a nucleus-substituted 1- or 2-naphthol, a pyrazolone or a nucleus-substituted pyrazolone or an acyclic or alicyclic β-diketone compound; and B represents a phenyl group, a nucleus-substituted phenyl group, a naphthyl group or a nucleus-substituted naphthyl group and Redox Moiety represents a group represented by the following general formula:

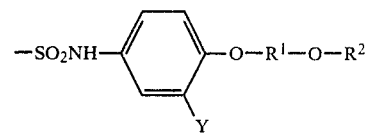

wherein $R^1$ represents an unsubstituted straight chain alkylene group having 2 or more carbon atoms or an unsubstituted branched chain alkylene group having 2 or more carbon atoms with the proviso the branched chain alkylene group is incapable of forming an acetal linkage; $R^2$ represents an alkyl group; and Y represents a o-hydroxyphenyl sulfamoyl group having a ballast group bonded thereto and an alkyl group at the meta position to the hydroxyl group thereof.

2. The photographic light-sensitive element as claimed in claim 1, wherein the dye moiety (D) is a group represented by the following formula (III):

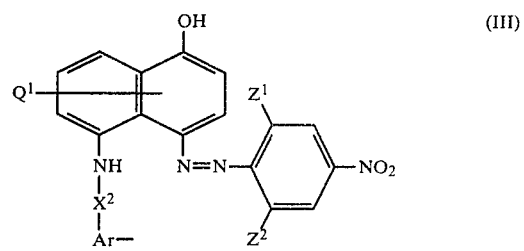

wherein $Q^1$, which can be present on either ring of the naphthol nucleus, represents a hydrogen atom, a halogen atom, a group represented by the formula —SO$_2$NR$^3$R$^4$, a group represented by the formula —SO$_2$R$^5$, a carboxy group, a group represented by the formula —COOR$^6$, or a group represented by the formula —CONR$^3$R$^4$; $R^3$ represents a hydrogen atom or a straight or branched chain alkyl group having 1 to 8 carbon atoms; $R^4$ represents a hydrogen atom or a straight or branched chain alkyl group having 1 to 8 carbon atoms, a straight or branched chain aralkyl group having 7 to 12 carbon atoms or a phenyl group; and $R^3$ and $R^4$ may combine directly or through an oxygen atom to form a ring; $R^5$ represents a straight or branched chain alkyl group having 1 to 8 carbon atoms or a straight or branched chain aralkyl group having 7 to 12 carbon atoms; $R^6$ represents a straight or branched chain alkyl group having 1 to 8 carbon atoms or a phenyl group; $X^2$ represents an —SO$_2$— group or a —CO— group; Ar represents a phenylene group; $Z^1$ represents a halogen atom, a cyano group, a nitro group, a trifluoromethyl group, a straight or branched chain alkyl group having 1 to 8 carbon atoms, a straight or branched chain alkoxy group having 1 to 8 carbon atoms, a carboxy group, a group represented by the formula —COOR$^6$, a fluorosulfonyl group, a phenoxysulfonyl group, a group represented by the formula —SO$_2$NR$^3$R$^4$, a group represented by the formula —CONR$^3$R$^4$, a straight or branched chain alkylsulfonyl group having 1 to 8 carbon atoms or a phenylsulfonyl group, wherein $R^3$, $R^4$ and $R^6$ each has the same meaning as defined above; $Z^2$ represents a hydrogen atom, a halogen atom, a nitro group, a cyano group or a trifluoromethyl group.

3. The photographic light-sensitive element as claimed in claim 2, wherein $R^1$ represents a —$CH_2CH_2$— group;

$R^2$ represents a straight chain or branched chain alkyl group having 1 to 4 carbon atoms;

$Q^1$, which is present at the 2-position with respect to the hydroxy group of the naphthalene ring, represents a hydrogen atom or a group represented by the formula —$SO_2NR^3R^4$, wherein $R^3$ and $R^4$, which may be the same or different, each represents an unsubstituted alkyl group having 1 to 4 carbon atoms or an alkyl group having 1 to 4 carbon atoms substituted with one or more of a cyano group, an alkoxy group, a hydroxy group, a carboxy group or a sulfo group, and $R^3$ and $R^4$ can combine directly or through an oxygen atom to form a 5- or 6-membered ring;

and $X^2$ represents an —$SO_2$— group;

Ar represents an m-phenylene group or a p-phenylene group;

$Z^1$ represents a chlorine atom, a fluorine atom, a bromine atom, a cyano group, a nitro group, a trifluoromethyl group, a fluorosulfonyl group, a group represented by the formula —$SO_2NHR^{11}$, wherein $R^{11}$ represents an unsubstituted alkyl group having 1 to 4 carbon atoms or an alkyl group having 1 to 4 carbon atoms substituted with one or more of a cyano group, an alkoxy group, a hydroxy group, a carboxy group or a sulfo group, an unsubstituted alkylsulfonyl group having 1 to 4 carbon atoms, an alkylsulfonyl group having 1 to 4 carbon atoms substituted with one or more of a cyano group, an alkoxy group, a hydroxy group, a carboxy group or a sulfo group, an unsubstituted phenylsulfonyl group, or a phenylsulfonyl group substituted with one or more of a hydroxy group, a halogen atom, a carboxy group, a sulfo group, or a sulfamoyl group; and $Z^2$ represents a hydrogen atom, a chlorine atom, a bromine atom or a fluorine atom.

4. The photographic light-sensitive element as claimed in claim 2, wherein $R^1$ represents a —$CH_2CH_2$— group;

$R^2$ represents a straight chain or branched chain alkyl group having 1 to 4 carbon atoms;

$Q^1$ represents a hydrogen atom;

and $X^2$ represents an —$SO_2$— group;

Ar represents an m-phenylene group;

$Z^1$ represents a chlorine atom, a bromine atom, a cyano group, a trifluoromethyl group, a nitro group or an alkylsulfonyl group having 1 to 4 carbon atoms; and $Z^2$ represents a hydrogen atom, a chlorine atom or a bromine atom.

5. The photographic light-sensitive element as claimed in claim 1, wherein the dye moiety is a group represented by the following formula (IV):

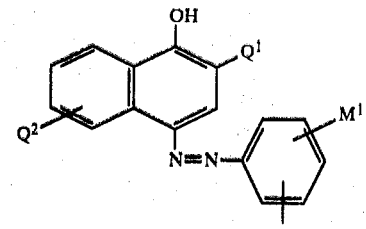

wherein $Q^1$ represents a hydrogen atom, a halogen atom, a group represented by the formula —$SO_2NR^3R^4$, a group represented by the formula —$SO_2R^5$, a carboxy group, a group represented by the formula —$COOR^6$, or a group represented by the formula —$CONR^3R^4$; $R^3$ represents a hydrogen atom or a straight or branched chain alkyl group having 1 to 8 carbon atoms; $R^4$ represents a hydrogen atom or a straight or branched chain alkyl group having 1 to 8 carbon atoms, a straight or branched chain aralkyl group having 7 to 12 carbon atoms or a phenyl group; and $R^3$ and $R^4$ may combine directly or through an oxygen atom to form a ring; $R^5$ represents a straight or branched chain alkyl group having 1 to 8 carbon atoms or a straight or branched chain aralkyl group having 7 to 12 carbon atoms; $R^6$ represents a straight or branched chain alkyl group having 1 to 8 carbon atoms or a phenyl group; $Q^2$, which can be positioned at the 5- or the 8-position to the hydroxy group, represents a hydroxy group, a group represented by the formula —$NHCOR^4$ or a group represented by the formula —$NHSO_2R^4$, wherein $R^4$ is as defined above except that $R^4$ is not a hydrogen atom; $M^1$ represents a hydrogen atom, a straight or branched chain alkyl group having 1 to 8 carbon atoms, a straight or branched chain alkoxy group having 1 to 8 carbon atoms or a halogen atom.

6. The photographic light-sensitive element as claimed in claim 5, wherein $R^1$ represents a —$CH_2CH_2$— group;

$R^2$ represents a straight chain or branched chain alkyl group having 1 to 4 carbon atoms;

$Q^1$ represents a hydrogen atom or a group represented by the formula —$SO_2NR^3R^4$, wherein $R^3$ and $R^4$, which may be the same or different, each represents an unsubstituted alkyl group having 1 to 4 carbon atoms or an alkyl group having 1 to 4 carbon atoms substituted with one or more of a cyano group, an alkoxy group, a hydroxy group, a carboxy group or a sulfo group, and $R^3$ and $R^4$ can combine directly or through an oxygen atom to form a 5- or 6-membered ring;

$Q^2$ is at the 5-position and represents a hydroxy group or a group represented by the formula —$NHSO_2R^4$, wherein $R^4$ represents an unsubstituted alkyl group having 1 to 4 carbon atoms or an alkyl group having 1 to 4 carbon atoms substituted with one or more of a cyano group, an alkoxy group, a hydroxy group, a carboxy group or a sulfo group; and $M^1$ represents a hydrogen atom, an unsubstituted alkyl group having 1 to 4 carbon atoms, an alkoxy group having 1 to 4 carbon atoms or a chlorine atom.

7. The photographic light-sensitive element as claimed in claim 5, wherein $R^1$ represents a —$CH_2CH_2$— group;

$R^2$ represents a straight chain or branched chain unsubstituted alkyl group having 1 to 4 carbon atoms;

$Q^1$ represents a group of the formula —$SO_2N(CH_2)_4$;

$Q^2$ represents a group represented by the formula —$NHSO_2$-alkyl, with the alkyl moiety having 1 to 4 carbon atoms, at the 5-position;

$M^1$ represents a methyl group or a hydrogen atom.

8. The photographic light-sensitive element as claimed in claim 1, wherein the dye moiety is a group represented by the following formula (V):

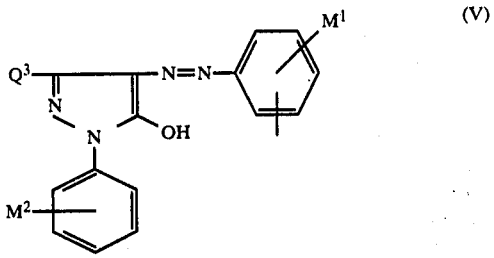

(V)

wherein $M^1$ represents a hydrogen atom, a straight or branched chain alkyl group having 1 to 8 carbon atoms, a straight or branched chain alkoxy group having 1 to 8 carbon atoms or a halogen atom; $M^2$ represents a hydrogen atom, a straight or branched chain alkyl group having 1 to 8 carbon atoms, a group represented by the formula —$SO_2NR^3R^4$ or a group represented by the formula —$COOR^6$; $R^3$ represents a hydrogen atom or a straight or branched chain alkyl group having 1 to 8 carbon atoms; $R^4$ represents a hydrogen atom or a straight or branched chain alkyl group having 1 to 8 carbon atoms, a straight or branched chain aralkyl group having 7 to 12 carbon atoms or a phenyl group; and $R^3$ and $R^4$ may combine directly or through an oxygen atom to form a ring; $R^6$ represents a straight or branched chain alkyl group having 1 to 8 carbon atoms or a phenyl group; and $Q^3$ represents a cyano group or a group represented by the formula —$CONR^3R^4$, and $R^3$ and $R^4$ each has the same meaning as defined above.

9. The photographic light-sensitive element as claimed in claim 8, wherein $R^1$ represents a —$CH_2CH_2$— group;

$R^2$ represents a straight chain or branched chain unsubstituted alkyl group having 1 to 4 carbon atoms;

$M^1$ represents a hydrogen atom, an unsubstituted alkyl group having 1 to 4 carbon atoms, an alkoxy group having 1 to 4 carbon atoms or a halogen atom;

$M^2$ represents a hydrogen atom or an unsubstituted alkyl group having 1 to 4 carbon atoms;

$Q^3$ represents a cyano group or a group represented by the formula —$CONR^3R^4$, wherein $R^3$ and $R^4$, which may be the same or different, each represents a hydrogen atom, an unsubstituted alkyl group having 1 to 4 carbon atoms or an alkyl group having 1 to 4 carbon atoms substituted with one or more of a cyano group, an alkoxy group, a hydroxy group, a carboxy group or a sulfo group, and $R^3$ and $R^4$ can combine directly or through an oxygen atom to form a 5- or 6-membered ring.

10. The photographic light-sensitive element as claimed in claim 8 wherein $R^1$ represents a —$CH_2CH_2$— group;

$R^2$ represents a straight chain or branched chain unsubstituted alkyl group having 1 to 4 carbon atoms;

$M^1$ represents a hydrogen atom, an unsubstituted alkyl group having 1 to 4 carbon atoms, an alkoxy group having 1 to 4 carbon atoms or a chlorine atom;

$M^2$ represents a hydrogen atom or an unsubstituted alkyl group having 1 to 4 carbon atoms;

$Q^3$ represents a cyano group.

11. The photographic light-sensitive element as claimed in claim 1, wherein $R^1$ represents a —$CH_2CH_2$— group.

12. The photographic light-sensitive element as claimed in claim 11, wherein $R^2$ represents an alkyl group having 1 to 4 carbon atoms.

13. The photographic light-sensitive element as claimed in claim 1, wherein the alkyl group bonded to the meta position of the o-hydroxyphenylsulfamoyl group is an alkyl group having 1 to 4 carbon atoms.

14. The photographic light-sensitive element as claimed in claim 1, wherein $R^1$ has 2 to 8 carbon atoms and $R^2$ has 1 to 8 carbon atoms.

15. The photographic light-sensitive element as claimed in claim 14, wherein $R^2$ is an unsubstituted alkyl group.

* * * * *